(12) United States Patent
Van Eijk et al.

(10) Patent No.: US 11,130,781 B2
(45) Date of Patent: Sep. 28, 2021

(54) ANTIMICROBIAL PEPTIDES AND THEIR USE

(71) Applicants: UNIVERSITEIT UTRECHT HOLDING B.V., Utrecht (NL); UMC UTRECHT HOLDING B.V., Utrecht (NL)

(72) Inventors: Marinus Van Eijk, Utrecht (NL); Albert Van Dijk, Zeist (NL); Hendrik Peter Haagsman, Zeist (NL); Cornelis Korstiaan Van Der Ent, Houten (NL)

(73) Assignees: Universiteit Utrecht Holding B.V., Utrecht (NL); UMC Utrecht Holding B.V., Utrecht (NL)

( * ) Notice: Subject to any disclaimer, the term of this patent is extended or adjusted under 35 U.S.C. 154(b) by 0 days.

(21) Appl. No.: 16/608,025

(22) PCT Filed: Apr. 24, 2018

(86) PCT No.: PCT/EP2018/060402
§ 371 (c)(1),
(2) Date: Oct. 24, 2019

(87) PCT Pub. No.: WO2018/197445
PCT Pub. Date: Nov. 1, 2018

(65) Prior Publication Data
US 2020/0190145 A1    Jun. 18, 2020

(30) Foreign Application Priority Data
Apr. 25, 2017 (EP) .................................. 17167981

(51) Int. Cl.
| C07K 7/08 | (2006.01) |
| A61P 31/12 | (2006.01) |
| A61P 31/04 | (2006.01) |
| A61K 38/00 | (2006.01) |

(52) U.S. Cl.
CPC ................ *C07K 7/08* (2013.01); *A61P 31/04* (2018.01); *A61P 31/12* (2018.01); *A61K 38/00* (2013.01)

(58) Field of Classification Search
CPC . C07K 7/08; A61P 31/12; A61P 31/04; A61K 38/00
See application file for complete search history.

(56) References Cited

U.S. PATENT DOCUMENTS

| 6,080,724 A | * | 6/2000 | Chassaing | ........ | C07K 14/43581 |
| | | | | | 514/1.2 |
| 8,927,502 B2 | * | 1/2015 | Bieker | ................. | C12N 15/113 |
| | | | | | 514/21.5 |

FOREIGN PATENT DOCUMENTS

| WO | WO 97/12912 | * 4/1997 | ............. C07K 14/47 |
| WO | 2006050611 A1 | 5/2006 | |
| WO | 2015161820 A1 | 10/2015 | |

OTHER PUBLICATIONS

De Bruijn et al., 2015, Comparative genomics and metabolic profiling of the genus *Lysobacter*, BMC Genomics, 16: 991 (16 pages).*

Dou, Xiujing, et al. "Novel Design of Heptad Amphiphiles to Enhance Cell Selectivity, Salt Resistance, Antibiofilm Properties and Their Membrane-Disruptive Mechanism." Journal of Medicinal Chemistry, vol. 60, No. 6, 2017, pp. 2257-2270.

Maniti, Ofelia, et al. "Basic Cell Penetrating Peptides Induce Plasma Membrane Positive Curvature, Lipid Domain Separation and Protein Redistribution." International Journal of Biochemistry Cell Biology, vol. 50, 2014, pp. 73-81.

PCT International Search Report and Written Opinion, Application No. PCT/EP2018/060402, dated Jun. 6, 2018, 11 pages.

Shagaghi, Nadin, et al. "Archetypal Tryptophan-Rich Antimicrobial Peptides: Properties and Applications." World Journal of Urology, vol. 32, No. 2, 2016, pp. 1-10.

* cited by examiner

*Primary Examiner* — Amber D Steele
(74) *Attorney, Agent, or Firm* — Patent Law Works LLP

(57) ABSTRACT

The invention relates to the field of antibiotics, more specifically to peptide antibiotics, such as antimicrobial peptides and their use in the treatment of diseases associated with microbial infections. In particular, the invention provides a peptide with antimicrobial activity comprising an amino acid sequence RRWVQRWIRRWR (SEQ ID NO: 24) or an analogue thereof.

8 Claims, 7 Drawing Sheets

Figure 1:
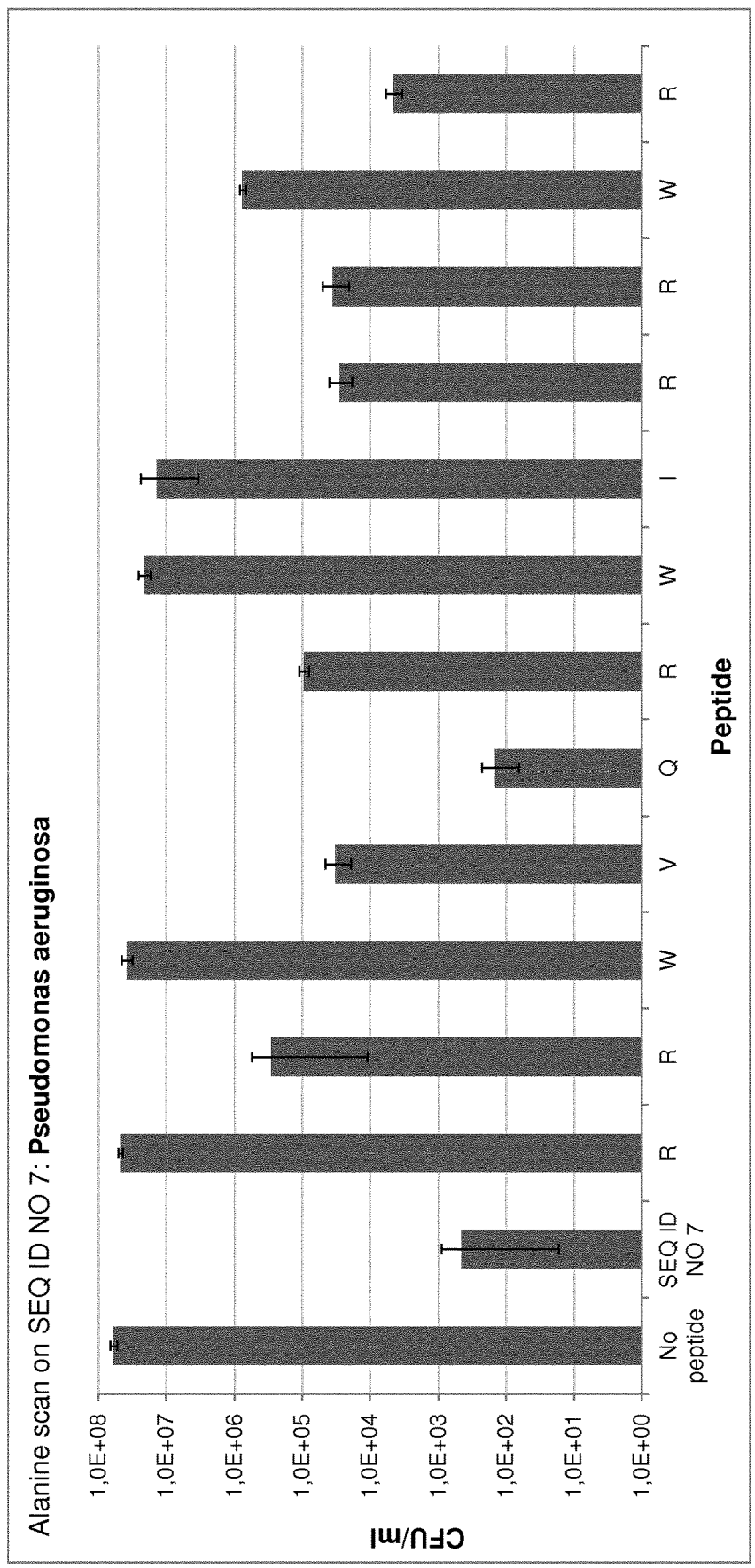

Specification includes a Sequence Listing.

ANTIMICROBIAL PEPTIDES AND THEIR USE

FIELD OF THE INVENTION

The invention relates to the field of antimicrobial agents, such as antibiotics, more specifically to antimicrobial peptides, such as peptide antibiotics and their use in the treatment of diseases associated with microbial infections.

BACKGROUND OF THE INVENTION

The ever increasing number of multi-drug resistant pathogens has urged the need for new antimicrobial agents, such as antibiotics. In the last decade, scientists have put much effort in the developments of novel antibacterial agents as well as improvement of current chemotherapeutic agents. Interestingly, many mammals and insects are remarkably resistant to bacterial infection, due to their ability to produce small-sized cationic peptides. This form of protection, an important part of the innate immune system, provides a first line of defense against invading pathogens. Many scientists have focused their attention on these antimicrobial peptides as they are currently regarded as an important pool of potentially novel antibiotics.

Thus far, many types of antimicrobial peptides have been isolated and sequenced from various sources during past decades (for selected reviews, see: Otvos Jr., L. Cell. Mol. Life Sci. 2002, 59:1138; Otvos, Jr., L. J. Peptide Sci. 2000, 6:497; Tan, Y. -T. et al., Mol. Med. Today 2000, 6:309; Scott, M. G. and Hancock, R. E. W., Crit. Rev. Immunol. 2000, 20:407; Hancock, R. E. W. and Chappie, D. S. Antimicrob. Agents Chemother. 1999, 43:1317; Hetru, C. et al., In: Molecular Mechanisms of Immune Responses in Insects; Brey, P. and Hultmark, D. Ed., Chapman and Hall, London, 1998, pp. 40-66; Hancock, R. E. W. et al., Adv. Microb. Physiol. 1995 37:135; Vaara, M. Microbiol. Rev).

Antimicrobial peptides may be used in a number of applications, such as in the treatment of a disease encompassing microbial infections, such as bacterial, fungal or viral infections.

Cystic fibrosis (CF) is the most common lethal autosomal recessive disorder in western countries, with a birth prevalence of 1:4,750 in The Netherlands. This life-threatening chronic lung disease is characterized by accumulation of pulmonary mucus and excessive microbial colonization that leads to chronic pulmonary inflammation. Lung damage secondary to chronic infection is the main determinant of morbidity and mortality in CF-patients. Currently, the mean life expectancy of patients with CF is about 35 years. The disease affects approximately 40,000 children and young adults in the European Union and a similar number in the United States.

Respiratory tract infections in CF start early in life. Recent data from Australian birth cohort studies show that at 3 months of age over 20% of patients is infected with CF-specific micro-organisms like *Staphylococcus aureus* and *Pseudomonas aeruginosa*, with increase of neutrophils and neutrophil elastase in broncho-alveolar lavage fluids (Sly, Gangell et al., 2013). At 3 years of age over 50% of patients is infected and more than 60 percent of patients show irreversible post-infectious pulmonary scarring. As patients grow older, they are progressively infected with micro-organisms preferentially associated with CF, as *Pseudomonas aeruginosa, Staphylococcus aureus, Hemophilus influenzae, Stenotrophomonas maltophilia, Achromobacter xylosoxidans*, and *Burholderia* species.

Despite recent advances in the art providing new antimicrobial agents, there remains a large demand for more specific, economic and/or more effective antimicrobial peptides suitable for the treatment of humans and animals with less side-effects.

SUMMARY OF THE INVENTION

We found that a peptide comprising the amino acid sequence RRWVQRWIRRWR (SEQ ID NO: 24) or an analogue thereof exhibited advantageous antimicrobial and/or antibacterial properties. The invention therefore relates to a peptide with antimicrobial activity comprising an amino acid sequence RRWVQRWIRRWR (SEQ ID NO: 24) or an analogue thereof.

Analogues of the peptides as presented herein may be obtained by methods known in the art wherein the amino acid sequence RRWVQRWIRRWR (SEQ ID NO: 24) is altered in such a way that one or more amino acids are replaced by one or more other amino acids such as natural amino acids.

The invention also relates to a pharmaceutical preparation comprising a peptide as described herein and a pharmaceutically acceptable carrier or excipient. Such a preparation may then be used as an antimicrobial or antibiotic agent, for instance in the treatment, prevention or amelioration of microbial infections in an animal.

DETAILED DESCRIPTION OF THE INVENTION

Antimicrobial peptides as such are known and may be used in a number of applications, such as in the treatment or prevention of a disease encompassing microbial infections, such as bacterial, fungal or viral infections.

An antimicrobial agent such as an antimicrobial peptide is an agent that kills microorganisms or inhibits or prevents their growth. Antimicrobial agents can be grouped according to the microorganisms they act primarily against. For example, antibiotics are used against bacteria, antivirals are used against viruses and antifungals are used against fungi.

Antibiotics, also called antibacterials, are a type of antimicrobial agents used in the treatment and prevention of bacterial infections. They may either kill or inhibit the growth of bacteria. A limited number of antimicrobial agents also possess antiprotozoal activity. Antimicrobials can also be classified according to their function. Agents that kill microbes are called microbicidal, while those that merely inhibit their growth are called biostatic. The use of antimicrobial agents to treat infection is also known as antimicrobial therapy, while the use of antimicrobial medicines to prevent infection is known as antimicrobial prophylaxis.

The main classes of antimicrobial agents are disinfectants ("nonselective antimicrobials" such as bleach), which kill a wide range of microbes on non-living surfaces to prevent the spread of illness, antiseptics (which are applied to living tissue and help reduce infection for example during surgery), and antibiotics (which may be used to destroy microorganisms within the body).

The term "antibiotic" originally only encompassed those formulations derived from living organisms but is now also applied to synthetic antimicrobials, such as the sulphonamides, or fluoroquinolones. The term also used to be restricted to antibacterials (and is often used as a synonym for them by medical professionals and in medical literature), but in modern literature its context has broadened to include all antimicrobials. Antibacterial agents can be further subdivided into bactericidal agents, which kill bacteria, and bacteriostatic agents, which slow down or stall bacterial growth.

Many antimicrobial peptides exist, and their use to combat microorganisms such as bacteria, viruses and fungi is well known in a wide range of infectious diseases.

The term "peptide" as used herein means a sequence of amino acids coupled by a peptide bond, wherein the amino acids are one of the twenty naturally peptide-building amino acids and wherein one or all of the amino acids can be in the L-configuration or in the D-configuration, or, for isoleucine and threonine in the D-allo configuration (only inversion at one of the chiral centers). A peptide according to the invention can be linear, i.e. wherein the first and last amino acids of the sequence have a free NH2- or COOH-group respectively or are N-terminally (acetylation) and/or C-terminally (amidation) modified. In a further embodiment, the peptide may be circular.

The terms "oligopeptide" and "polypeptide" are used to indicate short and long peptides respectively, wherein short means up to 20 amino acids, whereas long peptides means 20 amino acids or longer. The term "peptides" or "peptide" encompasses both oligopeptides as well as polypeptides.

The peptides of the invention can be produced synthetically or, where applicable, by recombinant DNA technology using conventional methods. Specific embodiments of antimicrobial peptides are disclosed in detail in the experimental part below. Preferably, the peptides of the invention are prepared conventionally by known chemical synthesis techniques, such as, for instance, disclosed by Merrifield (J. Am. Chem. Soc. (1963) 85:2149-2154). They may be isolated from the reaction mixture by chromatographic methods, such as reverse-phase HPLC.

Alternatively, the peptides of the invention may be produced by recombinant DNA techniques by cloning and expressing a DNA fragment, carrying a nucleic acid sequence encoding one of the above-described peptides, within a prokaryotic or eukaryotic cell. Nucleic acid coding sequences can be prepared synthetically, or may be derived from existing nucleic acid sequences by site-directed mutagenesis. These nucleic acid sequences may then be cloned in a suitable expression vector and transformed or transfected into a suitable host cell, such as *E. coli, Bacillus, Lactobacillus, Streptomyces*, mammalian cells (such as CHO, HEK or COS-1 cells), yeasts (e.g. *Saccharomyces*), fungi (e.g. *Aspergillus*), insect cells or viral expression systems, such as baculovirus systems, or plant cells. A person skilled in the art will have knowledge of the techniques of constructing the nucleic acid sequences and providing means to enable their expression.

More in particular, plant cells could be used advantageously for expression of the peptides of the invention, since the peptide in such a case could orally be administered to a human or animal directly, i.e. without any further purification.

Subsequently, the peptide can be isolated from the culture of a host cell. This can be achieved by common protein purification and isolation techniques, which are available in the art. Such techniques may e.g. involve immune-adsorption or chromatography. It is also possible to provide the peptides with a tag (such as a histidine tag) during synthesis, which allows for rapid affinity purification, after which the tag is enzymatically removed to obtain the active peptide.

Alternatively, the peptides can be produced in cell-free systems, such as the Expressway™ cell-free system of Invitrogen. More comprehensive summaries of methods which can be applied in the preparation of the peptides are described in: W. F. Anderson, Nature 392 Supp., 30 Apr. 1998, p. 25-30; Pharmaceutical Biotechnology, Ed. D. J. A. Crommelin and R. D. Sindelar, Harwood Academic Publishers, 1997, p. 53-70, 167-180, 123-152, 8-20; Protein Synthesis: Methods and Protocols, Ed. R. Martin, Humana Press, 1998, p. 1-442; Solid-Phase Peptide Synthesis, Ed. G. B. Fields, Academic Press, 1997, p. 1-780; Amino Acid and Peptide Synthesis, Oxford University Press, 1997, p. 1-89.

Novel peptides as disclosed herein can thus be readily made by a person skilled in the art. All peptides described and exemplified herein were synthesized by the custom peptide synthesis service ChinaPeptides; http://www.chinapeptides.com/indexe.php. All peptides were amidated at the C-terminus to increase their stability, with the exception of the peptide with SEQ ID NO: 15.

Peptides were tested for their antibacterial activity in a killing assay using several different media for clinically relevant bacterial strains as described in Example 1. It was found that all peptides comprising the amino acid sequence RRWVQRWIRRWR (SEQ ID NO: 24) were active against bacteria isolated from cystic fibrosis patients, such as *Pseudomonas aeruginosa* or *Staphylococcus aureus*, or both. The results of the assay are shown in table 1.

TABLE 1

Antibacterial activity of peptides as described herein(*)

| SEQ ID NO: | Amino Acid Sequence | Pseudomonas aeruginosa | Staphylococcus aureus |
|---|---|---|---|
|  | No peptide control | 0 | 0 |
| 1 | LLGDFFRKSKEKIGKEFKRIVQRIKDFLRNLVPRTES | +++ | + |
| 2 | RFGRFLRKIRRFRPKVTITIQGSARF | ++++ | ++++ |
| 3 | RRWVQRWIRRWRPKV | ++++ | ++ |
| 4 | RRWVQRWIRRWRKV | ++++ | 0 |
| 5 | RRWVQRWIRRWRKPV | ++++ | 0 |
| 6 | RRWVQRWIRRWRPWV | ++++ | 0 |
| 7 | RRWVQRWIRRWRKWV | ++++ | ++++ |
| 8 | RRWVQRWIRRWRPK | ++++ | + |
| 9 | RRWVQRWIRRWRPKW | ++++ | ++ |
| 10 | RRWVQRWIRRWRPKVAAARRWV | ++++ | ++++ |
| 11 | RRWVQRWIRRWRPKRIVQRIKDFLRNLV | ++++ | ++++ |
| 12 | RRWVQRWIRRWRPKVAAARRWVQRWIRRWRPKV | ++++ | ++++ |
| 13 | RRWVQRWIRRWRKVAAARRWVQRWIRRWRPKV | ++++ | ++++ |
| 14 | RRWVQRWIRRWRPKVLQKKGI | ++++ | + |
| 15 | RRWVQRWIRRWRPKVLQKKGI | ++ | 0 |
| 16 | RRWVQRWIRRWRPKLQKKGI | ++++ | + |
| 17 | APKAMRRWVQRWIRRWRPR | ++++ | ++ |

TABLE 1-continued

Antibacterial activity of peptides as described herein(*)

| SEQ ID NO: | Amino Acid Sequence | Pseudomonas aeruginosa | Staphylococcus aureus |
|---|---|---|---|
| | V | | |
| 18 | APKAMRRWVQRWIRRWRPKVLQKKGI | ++++ | + |
| 19 | APKAMRRWVQRWIRRWRPRLQKKGI | ++++ | + |
| 20 | APKAMRRWVQRWIRRWRPLQKKGI | ++++ | + |
| 21 | APKAMRRWVQRWIRRWRPKVLQKNNYL | ++++ | + |
| 22 | APKAMRRWVQRWIRRWRPKVFQVTGSSA | ++++ | 0 |
| 23 | APKAMRRWVQRWIRRWRPKVLLHYPSQKF | ++++ | +++ |
| 24 | RRWVQRWIRRWR | n.a. | n.a. |
| 25 | RRWVRRWIRRWRPKV | ++++ | ++ |
| 26 | APKAMRWVQRWIRRWRPKLQKKGI | ++++ | + |
| 27 | APKAMWVQRWIRRWRPLQKKGI | ++ | 0 |

(*)Killing efficacy of peptides was determined in MHB medium and defined as follows:
"0", no killing;
"+", 0-100 fold reduction in Colony Forming Units (CFU's) after treatment;
"++", 100-1.000 fold;
"+++"; 1.000-100.000 fold;
"++++", no CFU's detected after treatment;
n.a. not analyzed.

It was found that the peptides comprising the amino acid sequence RRWVQRWIRRWR (SEQ ID NO: 24) as disclosed herein are active against Gram-negative as well as Gram-positive bacteria when tested in MHB medium. These results are shown in table 1. The activity against Gram-negative bacteria such as Pseudomonas aeruginosa was in general somewhat more pronounced as compared with the activity against Gram-positive bacteria such as Staphylococcus aureus. In general, the antimicrobial activity of a large number of peptides as shown in Table 1 equaled the activity of the prior art peptide CMAP27 according to SEQ ID NO: 2, and surpassed the activity of prior art cathelicidin peptide LL-37 according to SEQ ID NO: 1.

The findings as presented herein should not be interpreted so narrowly that no modifications are allowed in the amino acid sequence RRWVQRWIRRWR (SEQ ID NO: 24). We tested several peptides (SEQ ID NOs: 25-27) wherein one or two amino acids were altered. Such peptides still exhibited antimicrobial activity (table 1), albeit less than the peptides comprising the amino acid sequence RRWVQRWIRRWR (SEQ ID NO: 24).

Hence, the invention also relates to analogues of peptides comprising the amino acid sequence RRWVQRWIRRWR (SEQ ID NO: 24), wherein analogues means peptides comprising an amino acid sequence that differs in one or two amino acids from the amino acid sequence RRWVQRWIRRWR (SEQ ID NO: 24).

Such analogues may be prepared by a skilled person using recombinant DNA methods, or by synthetic peptide synthesis. Site-directed mutagenesis is a particularly preferred method for preparing analogues of the peptides disclosed herein. It is inevitable that such a procedure will occasionally also yield inactive peptides or peptides with less desirable properties. However, peptides with the desired properties may be selected easily and without any burden by the skilled person, employing the tests for antibacterial activity as disclosed herein.

A particularly suited method for finding analogues of the peptides as disclosed herein is a so-called alanine scan or Ala-scan, wherein one single amino acid residue of a (poly) peptide is replaced by an alanine residue, repeated for all or some of the individual amino acids of that peptide.

In molecular biology, alanine scanning is a technique used to determine the contribution of a specific residue to the stability or function of given protein. Alanine is used because of its non-bulky, chemically inert, methyl functional group that nevertheless mimics the secondary structure preferences that many of the other amino acids possess. Other amino acids such as valine or leucine may also be used in cases where conservation of the size of mutated residues is needed.

This technique can also be used to determine whether the side chain of a specific amino acid residue plays a significant role in bioactivity. This may also be accomplished by site-directed mutagenesis or random mutagenesis by creating a PCR library.

The technology is very mature at this point and is widely used in biochemical fields. It determines which residues in a given amino acid sequence may be changed while maintaining activity, or even which amino acids may be changed to alter the activity. This alteration may be an improvement, such as an increased activity or a more specific activity, depending on what is desired. After having established the site of the possible alteration, this site may be replaced with another amino acid, such as a natural amino acid, a non-natural amino acid or a modified one.

Accordingly, we performed an alanine scan of one of the most active peptides (SEQ ID NO: 7). The antimicrobial activity of the peptide consisting of the amino acid sequence according to SEQ ID NO: 7 (in short; peptide #7 or peptide 7) was compared to the antimicrobial activity of analogues of peptide #7 wherein one amino acid selected from the region of peptide 7 defined by SEQ ID NO: 24 was consecutively replaced by an alanine residue. These peptides are shown in table 7 below.

TABLE 7

Ala scan of peptide #7

| SEQ ID NO: | Amino Acid Sequence |
|---|---|
| 7 | RRWVQRWIRRWRKWV |
| 28 | ARWVQRWIRRWRKWV |
| 29 | RAWVQRWIRRWRKWV |
| 30 | RRAVQRWIRRWRKWV |
| 31 | RRWAQRWIRRWRKWV |
| 32 | RRWVARWIRRWRKWV |
| 33 | RRWVQAWIRRWRKWV |
| 34 | RRWVQRAIRRWRKWV |
| 35 | RRWVQRWARRWRKWV |

TABLE 7-continued

Ala scan of peptide #7

| SEQ ID NO: | Amino Acid Sequence |
|---|---|
| 36 | RRWVQRWI<u>A</u>RWRKWV |
| 37 | RRWVQRWIR<u>A</u>WRKWV |
| 38 | RRWVQRWIRR<u>A</u>RKWV |
| 39 | RRWVQRWIRRW<u>A</u>KWV |

It was found that the Tryptophan residues within the sequence RRWVQRWIRRWR (SEQ ID NO: 24) were essential for antimicrobial activity of the peptide.

In this context, the term "essential" as used herein indicates an amino acid residue that cannot be replaced by another amino acid such as an alanine residue, without a substantial loss of antimicrobial activity of the peptide against *Pseudomonas aeruginosa* as well as *Staphylococcus aureus*. Depending on the specific application and desired properties of such a peptide, it may however still be useful as a peptide with antimicrobial activity.

The term "substantial loss" in the context of an ala-substituted peptide means that the ala-substituted peptide shows an anti-microbial activity expressed in CFU/ml, that is at least three log scales less active than the unsubstituted peptide, i.e. peptide #7. For example, peptide #7 has an antimicrobial activity of 3.04 E+03 against *Staphylococcus aureus*, whereas the same peptide wherein the first tryptophan residue is replaced by an alanine, has an antimicrobial activity of 2.40 E+07 which is at least 3 log scales less active than peptide #7.

Figure 2:
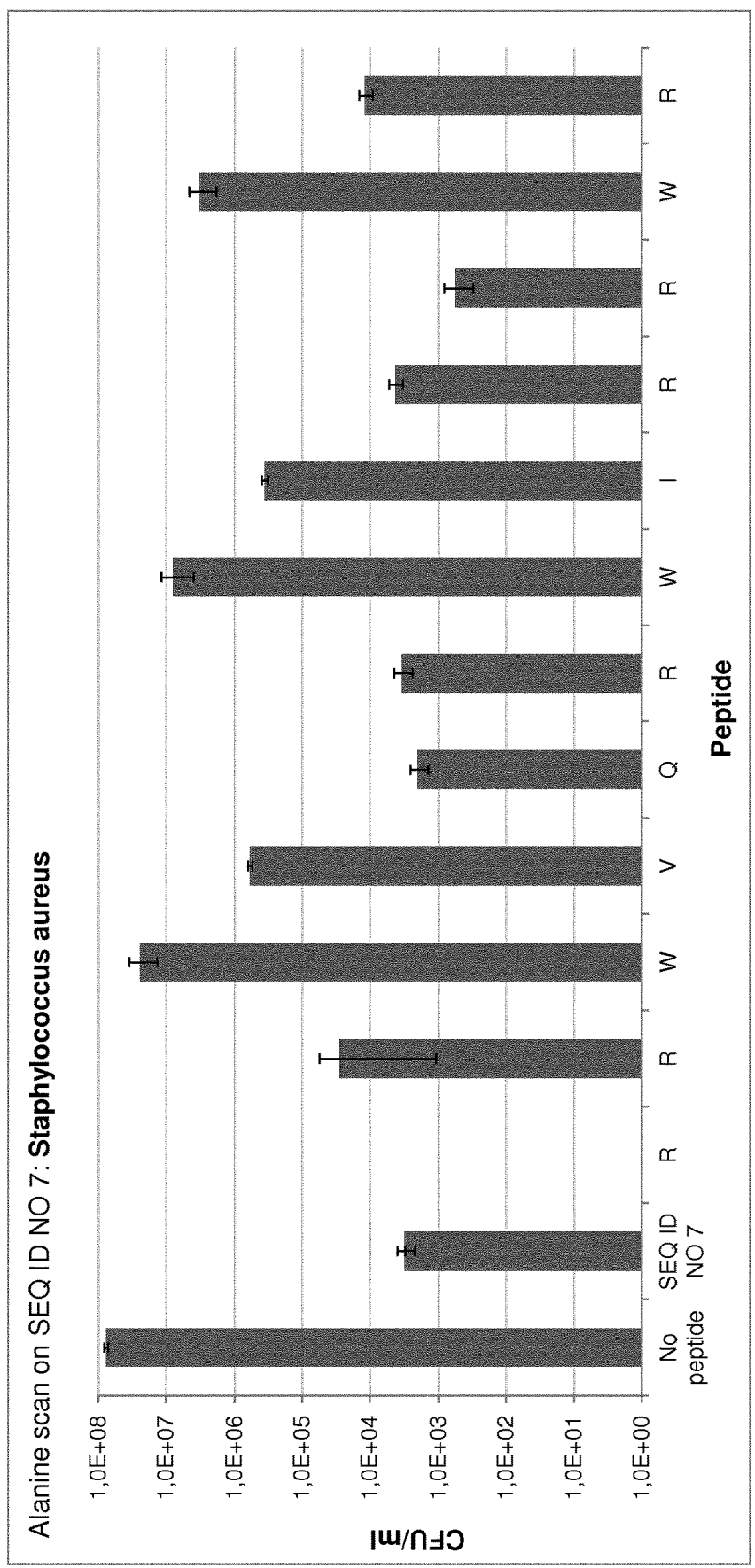
Figure 3:
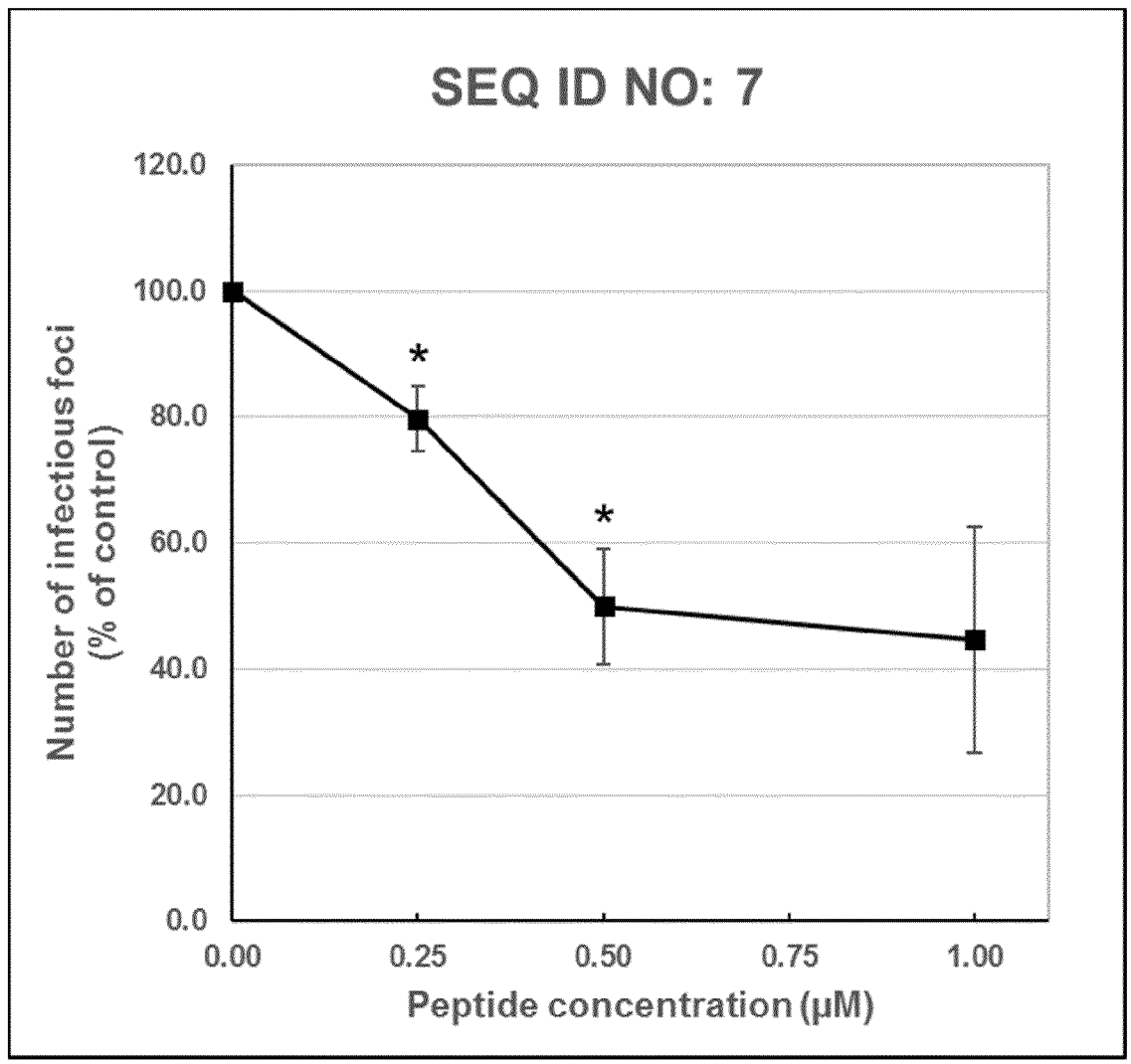
Figure 4:
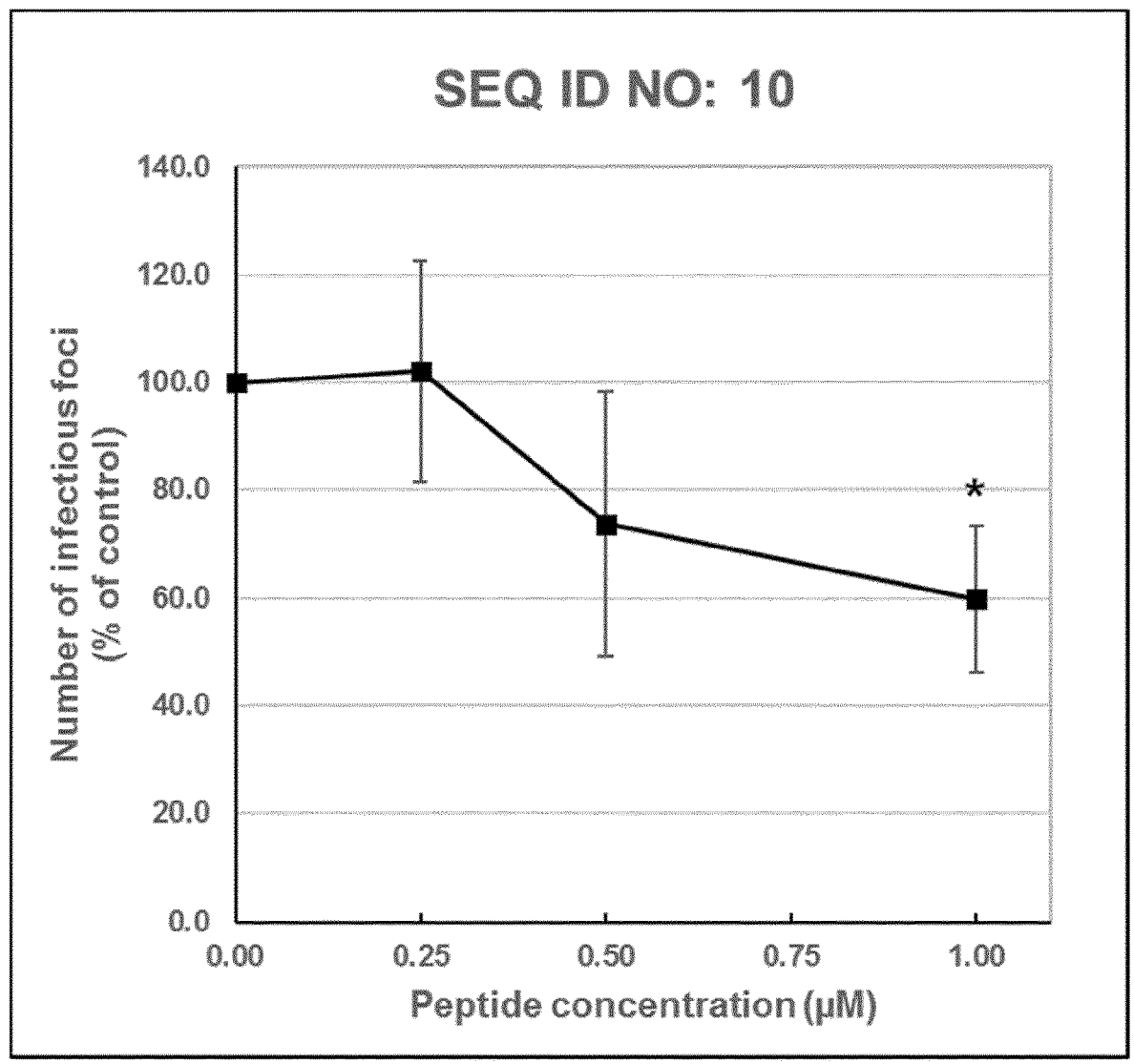
Figure 5:
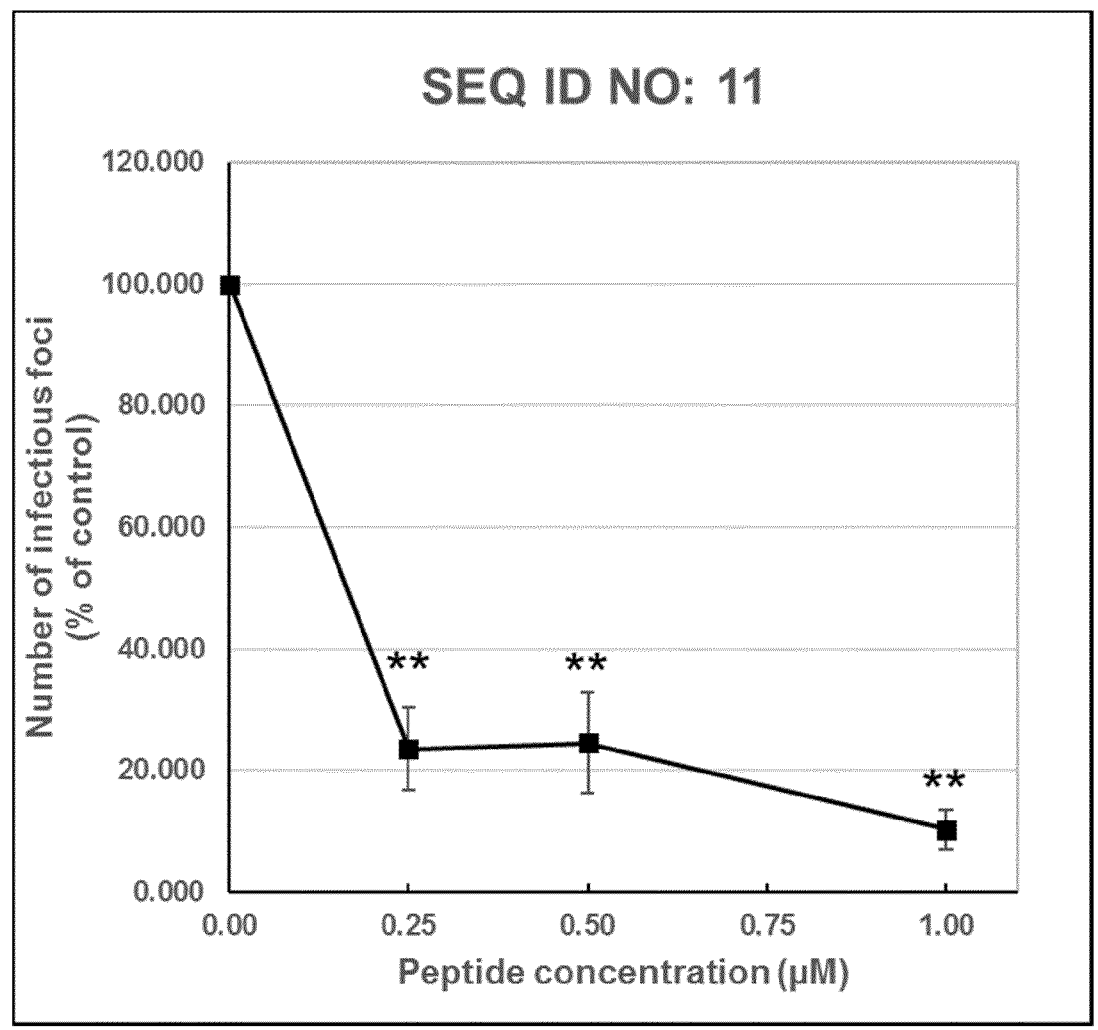
Figure 6:
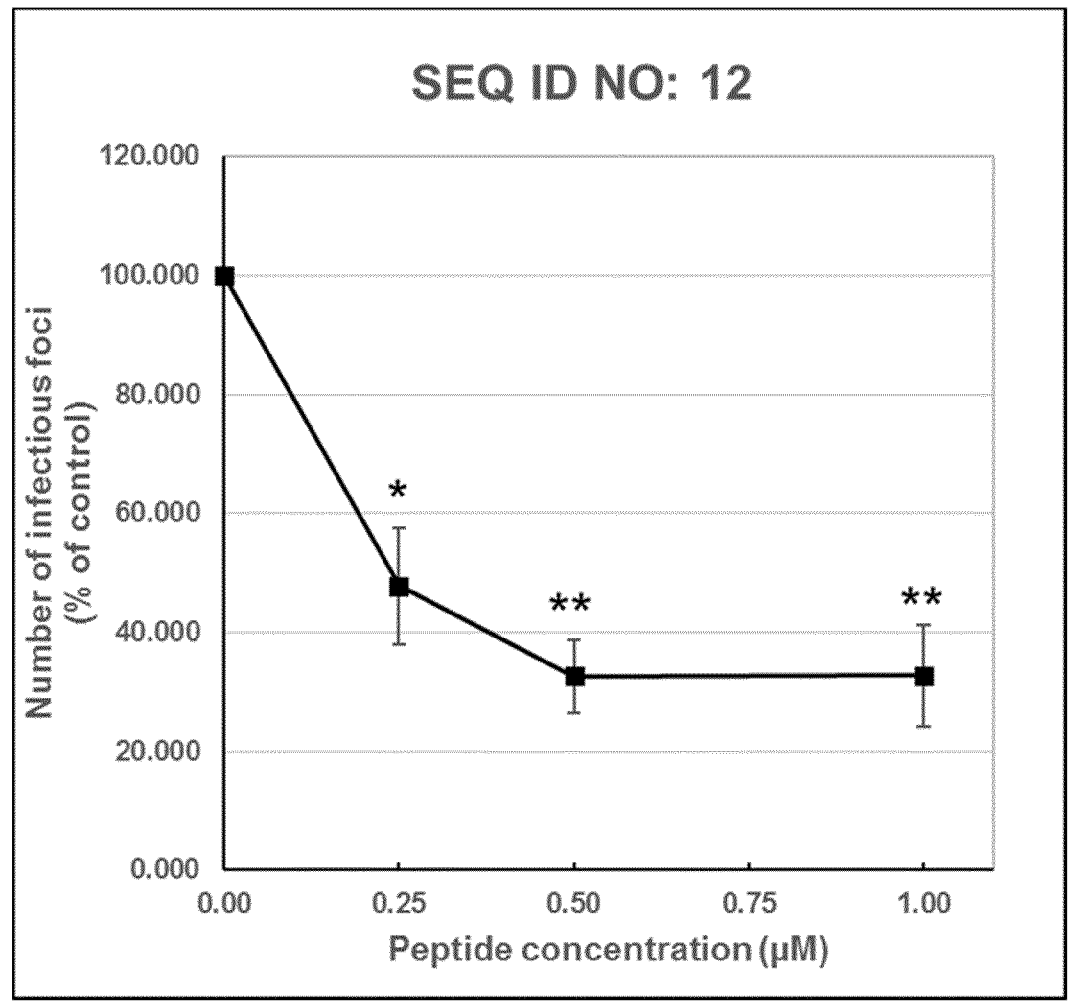
Figure 7:
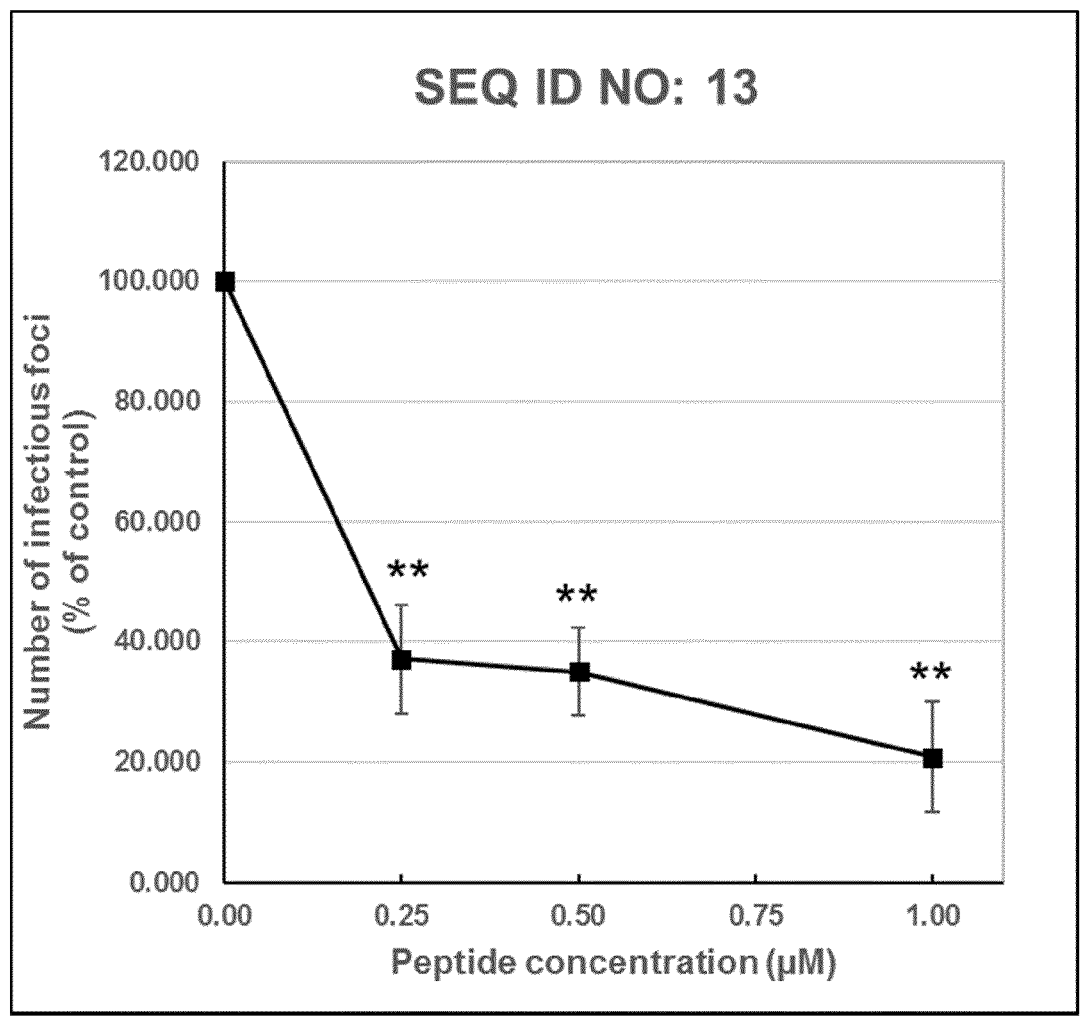

These results are shown in FIG. 1 and FIG. 2. Replacement of any of the other (non-tryptophan) amino acids in the core sequence RRWVQRWIRRWR (SEQ ID NO: 24) did not result in a substantial loss of antimicrobial activity against both *Staphylococcus aureus* and *Pseudomonas aeruginosa* and those non-tryptophan amino acids may therefore each individually be altered while maintaining antimicrobial activity.

Preferred analogues of the peptides as described herein may therefore be obtained by altering one of the non-tryptophan amino acids in SEQ ID NO: 24.

Analogues wherein two amino acids are altered in SEQ ID NO: 24 (such as for example peptide 27) are also described herein. In SEQ ID NO: 27 the first two arginine amino acids were altered and the peptide remained weakly active as an antifungal or antibacterial peptide (tables 3 and 4). It was also weakly toxic (table 5) and therefore may be useful in the treatment of bacterial diseases, infections or in the prevention thereof. The invention therefore also relates to a peptide as described herein wherein the amino acid according to SEQ ID NO: 24 is altered at two positions.

Further preferred analogues of the peptides as described herein may therefore be obtained by altering two of the non-tryptophan amino acids in SEQ ID NO: 24.

Interestingly, we observed that the replacement of the first amino acid residue in peptide 7 (Arginine) with an alanine residue resulted in an analogue of peptide 7 with different activity against Gram-positive and Gram-negative bacteria. It was observed that this analogue exhibited a largely increased activity (as compared to peptide 7) against *Staphylococcus aureus*, in that bacterial growth of *Staphylococcus aureus* was completely abolished after 3 hours. In steep contrast, this analogue was not active against *Pseudomonas aeruginosa* (FIG. 1).

We have shown therewith that it is possible to develop anti-microbial peptides with a differential activity against Gram-positive and Gram-negative bacteria.

Hence, the invention relates to a peptide with antimicrobial activity comprising an amino acid sequence RRWVQRWIRRWR (SEQ ID NO: 24) or an analogue thereof.

The peptides according to the invention may vary in length. They can be extended at both the N-terminal side as well as the C-terminal side as is evidenced by the peptides shown in table 1.

In a particularly preferred embodiment, the invention relates to a peptide comprising the general amino acid sequence X1-X2-X3, wherein X1 is 0-5 amino acids, X2 is an amino acid sequence consisting of the amino acid sequence RRWVQRWIRRWR according to SEQ ID NO: 24, and X3 is 2-21 amino acids.

In a further preferred embodiment, the invention relates to a peptide comprising the general amino acid sequence Y1-Y2-Y3, wherein Y1 is 0-5 amino acids, Y2 is an amino acid sequence that differs from the amino acid sequence RRWVQRWIRRWR according to SEQ ID NO: 24 by at most one or two amino acids, and Y3 is 2-21 amino acids.

In a further preferred embodiment, the invention relates to a peptide comprising the general amino acid sequence Z1-Z2-Z3, wherein Z1 is 0-5 amino acids, Z2 is an amino acid sequence that differs from the amino acid sequence RRWVQRWIRRWR according to SEQ ID NO: 24 by at most one or two amino acids, with the proviso that at least one of the tryptophan residues in Z2 is maintained at its original position, and Z3 is 2-21 amino acids.

The expression "at least one" in this context means one, two or all three tryptophan residues of SEQ ID NO: 24.

The expression "at its original position" refers to positions 3, 7 and 11 relative to the sequence of SEQ ID NO: 24. For example, a peptide comprising the sequence XX<u>W</u>XXX<u>W</u>XXX<u>W</u>X wherein X is any amino acid, fulfills the condition that a tryptophan residue is maintained at its original position relative to the sequence RRWVQRWIRRWR according to SEQ ID NO: 24.

The findings as disclosed herein make the peptides particularly useful as therapeutic agents, such as for instance in the treatment of infectious diseases. We therefore tested whether the peptides remained active in an environment that resembled the in vivo situation in humans and animals. For that purpose, we tested the antimicrobial activity of the same set of peptides in a eukaryotic cell medium; Bronchial Epithelial Cell Growth Medium (BEPC, Lonza), as well as in a bacterial medium (Mueller Hinton Broth, MHB) containing 0.9% NaCl at two different pH values (7.4 and 6.5), essentially as described in Example 1. The results are shown in Table 2

We found that these media all defined distinct microbial environments, since the antimicrobial activity of the peptides varied between the three different media (Table 2).

All of the peptides tested, exhibited antimicrobial activity in at least one of the conditions applied. This confirmed the above conclusion that the peptides according to the invention are useful as therapeutic agents.

This notion was again confirmed when we applied the bioscreen assay (Example 2) to the peptides listed in Tables 1 and 2. The results, shown in Table 3 confirm the outcome of the previous assays in that the peptides comprising the amino acid sequence RRWVQRWIRRWR (SEQ ID NO: 24) or analogues thereof were active as antimicrobial agents, whereas the overall activity against Gram-negative bacteria was slightly higher than the activity against Gram-positive bacteria.

TABLE 2

Antibacterial activity of peptides in media mimicking in vivo conditions(*).

| SEQ ID NO: | Amino Acid Sequence | Antibacterial activity | | | | | |
|---|---|---|---|---|---|---|---|
| | | Pseudomonas aeruginosa | | | Staphylococcus aureus | | |
| | | BEPC | NaCl 7.4 | NaCl 6.5 | BEPC | NaCl 7.4 | NaCl 6.5 |
| | No peptide control | 0 | 0 | 0 | 0 | 0 | 0 |
| 1 | LLGDFFRKSKEKIGKEFKRIVQRIKDFLRNLVPRTES | ++ | ++ | +++ | ++ | 0 | 0 |
| 2 | RFGRFLRKIRRFRPKVTITIQGSARF | ++++ | ++++ | ++++ | ++++ | ++++ | ++++ |
| 3 | RRWVQRWIRRWRPKV | 0 | 0 | 0 | ++ | 0 | 0 |
| 4 | RRWVQRWIRRWRKV | 0 | ++ | 0 | ++ | 0 | 0 |
| 5 | RRWVQRWIRRWRKPV | 0 | 0 | 0 | + | 0 | 0 |
| 6 | RRWVQRWIRRWRPWV | ++++ | ++ | 0 | ++++ | 0 | 0 |
| 7 | RRWVQRWIRRWRKWV | ++ | ++++ | +++ | ++++ | +++ | ++ |
| 8 | RRWVQRWIRRWRPK | + | + | 0 | + | 0 | 0 |
| 9 | RRWVQRWIRRWRPKW | + | + | 0 | +++ | 0 | 0 |
| 10 | RRWVQRWIRRWRPKVAAARRWV | ++++ | ++++ | ++ | ++++ | ++ | 0 |
| 11 | RRWVQRWIRRWRPKRIVQRIKDFLRNLV | ++++ | ++++ | ++ | ++++ | +++ | ++ |
| 12 | RRWVQRWIRRWRPKVAAARRWVQRWIRRWRPKV | ++++ | ++++ | ++++ | ++++ | ++++ | ++++ |
| 13 | RRWVQRWIRRWRKVAAARRWVQRWIRRWRPKV | ++++ | ++++ | ++++ | ++++ | ++++ | ++++ |
| 14 | RRWVQRWIRRWRPKVLQKKGI | + | + | 0 | ++ | 0 | 0 |
| 15 | RRWVQRWIRRWRPKVLQKKGI | + | 0 | 0 | ++ | 0 | 0 |
| 16 | RRWVQRWIRRWRPKLQKKGI | + | + | 0 | ++ | 0 | 0 |
| 17 | APKAMRRWVQRWIRRWRPRV | ++++ | +++ | + | ++++ | 0 | 0 |
| 18 | APKAMRRWVQRWIRRWRPKVLQKKGI | ++++ | +++ | + | ++++ | 0 | 0 |
| 19 | APKAMRRWVQRWIRRWRPRLQKKGI | ++++ | +++ | + | ++++ | 0 | 0 |
| 20 | APKAMRRWVQRWIRRWRPLQKKGI | ++++ | + | + | ++++ | 0 | 0 |
| 21 | APKAMRRWVQRWIRRWRPKVLQKNNYL | ++++ | +++ | ++ | ++++ | 0 | 0 |
| 22 | APKAMRRWVQRWIRRWRPKVFQVTGSSA | ++++ | ++ | 0 | ++++ | 0 | 0 |
| 23 | APKAMRRWVQRWIRRWRPKVLLHYPSQKF | ++++ | ++++ | ++ | ++ | + | 0 |
| 25 | RRWVRRWIRRWRPKV | + | + | 0 | +++ | 0 | 0 |
| 26 | APKAMRRWVQRWIRRWRPKLQKKGI | +++ | + | + | ++++ | 0 | 0 |
| 27 | APKAMWVQRWIRRWRPLQKKGI | 0 | 0 | 0 | + | 0 | 0 |

(*)Killing efficacy of peptides was determined and defined as follows:
"0", no killing;
"+", 0-100 fold reduction in Colony Forming Units(CFU's) after treatment;
"++", 100-1.000 fold;
"+++"; 1.000-100.000 fold;
"++++", no CFU's detected after treatment.

TABLE 3

Antibacterial activity as measured in the Bioscreen assay.

| SEQ ID NO: | Amino Acid Sequence | Bioscreen MIC values (µM) | |
|---|---|---|---|
| | | Pseudomonas aeruginosa | Staphylococcus aureus |
| 1 | LLGDFFRKSKEKIGKEFKRIVQRIKDFLRNLVPRTES | nd | nd |
| 2 | RFGRFLRKIRRFRPKVTITIQGSARF | 1.25 | 1.25 |
| 4 | RRWVQRWIRRWRKV | 5 | >10 |
| 6 | RRWVQRWIRRWRPWV | 2.5 | 10 |
| 7 | RRWVQRWIRRWRKWV | 1.25 | 2.5 |
| 8 | RRWVQRWIRRWRPK | 10 | >10 |
| 9 | RRWVQRWIRRWRPKW | 5 | 10 |
| 10 | RRWVQRWIRRWRPKVAAARWV | 1.25 | 10 |
| 11 | RRWVQRWIRRWRPKRIVQRIKDFLRNLV | 1.25 | 2.5 |
| 12 | RRWVQRWIRRWRPKVAAARRWVQRWIRRWRPKV | 1.25 | 1.25 |
| 13 | RRWVQRWIRRWRKVAAARRWVQRWIRRWRPKV | 1.25 | 1.25 |
| 14 | RRWVQRWIRRWRPKVLQKKGI | 10 | >10 |
| 16 | RRWVQRWIRRWRPKLQKKGI | 10 | >10 |
| 17 | APKAMRRWVQRWIRRWRPRV | 5 | >10 |
| 18 | APKAMRRWVQRWIRRWRPKVLQKKGI | 5 | >10 |

TABLE 3-continued

Antibacterial activity as measured in the Bioscreen assay.

| SEQ ID NO: | Amino Acid Sequence | Bioscreen MIC values (µM) Pseudomonas aeruginosa | Staphylococcus aureus |
|---|---|---|---|
| 19 | APKAMRRWVQRWIRRWRPRLQKKGI | 5 | >10 |
| 20 | APKAMRRWVQRWIRRWRPLQKKGI | 10 | >10 |
| 21 | APKAMRRWVQRWIRRWRPKVLQKNNYL | 2.5 | >10 |
| 22 | APKAMRRWVQRWIRRWRPKVFQVTGSSA | 10 | >10 |
| 23 | APKAMRRWVQRWIRRWRPKVLLHYPSQKF | 2.5 | >10 |
| 25 | RRWVRRWIRRWRPKV | 5 | >10 |
| 26 | APKAMRWVQRWIRRWRPKLQKKGI | 10 | >10 |
| 27 | APKA̱MWVQRWIRRWRPLQKKGI | >10 | >10 |

Again, a further selection of the peptides as disclosed herein was tested for their activity against fungi as described in Example 3. The results are shown in Table 4.

TABLE 4

Antifungal activity of peptides(*)

| SEQ ID NO: | Amino Acid Sequence | Antifungal activity |
|---|---|---|
|  | No peptide control | 0 |
| 1 | LLGDFFRKSKEKIGKEFKRIVQRIKDFLRNLVPRTES | + |
| 2 | RFGRFLRKIRRFRPKVTITIQGSARF | ++ |
| 4 | RRWVQRWIRRWRKV | 0 |
| 5 | RRWVQRWIRRWRKPV | 0 |
| 6 | RRWVQRWIRRWRPWV | 0 |
| 7 | RRWVQRWIRRWRKWV | 0 |
| 8 | RRWVQRWIRRWRPK | 0 |
| 9 | RRWVQRWIRRWRPKW | 0 |
| 10 | RRWVQRWIRRWRPKVAAARRWV | + |
| 11 | RRWVQRWIRRWRPKRIVQRIKDFLRNLV | ++ |
| 12 | RRWVQRWIRRWRPKVAAARRWVQRWIRRWRPKV | ++++ |
| 13 | RRWVQRWIRRWRKVAAARRWVQRWIRRWRPKV | ++++ |
| 14 | RRWVQRWIRRWRPKVLQKGI | + |
| 16 | RRWVQRWIRRWRPKLQKKGI | ++ |

TABLE 4-continued

Antifungal activity of peptides(*)

| SEQ ID NO: | Amino Acid Sequence | Antifungal activity |
|---|---|---|
| 17 | APKAMRRWVQRWIRRWRPRV | + |
| 18 | APKAMRRWVQRWIRRWRPKVLQKKGI | ++ |
| 19 | APKAMRRWVQRWIRRWRPRLQKKGI | +++ |
| 20 | APKAMRRWVQRWIRRWRPLQKKGI | +++ |
| 21 | APKAMRRWVQRWIRRWRPKVLQKNNYL | ++++ |
| 22 | APKAMRRWVQRWIRRWRPKVFQVTGSSA | +++ |
| 23 | APKAMRRWVQRWIRRWRPKVLLHYPSQKF | ++ |
| 25 | RRWVRRWIRRWRPKV | 0 |
| 26 | APKAMRWVQRWIRRWRPKLQKKGI | + |
| 27 | APKA̱MWVQRWIRRWRPLQKKGI | + |

*Relative potency of peptides to inhibit the metabolic activity of fungal spores (Killing efficacy) was defined as follows:
"0", no inhibition;
"+", 0-25% reduction in metabolic activity;
"++", 25-50%;
"+++", 50-75%;
"++++", 75-100%.

In addition to their antibacterial activity, some of the peptides appeared to have antifungal activity, some even more than the prior art peptides according to SEQ ID NO: 1 and SEQ ID NO: 2.

The invention therefore also relates to a peptide for use in the treatment of a disease caused or worsened by a fungus, such as *Aspergillus fumigatus*. A prime example of such a disease is cystic fibrosis.

An antimicrobial peptide is particularly suited for treatment of a human or animal when it has a low toxicity, combined with a high antimicrobial activity. We therefore tested the toxicity of the peptides as disclosed herein, as described in Example 4. Therein, the toxicity of the peptides was tested in primary human nasal epithelial cells. The results are shown in Table 5.

TABLE 5

Toxicity of selected peptides.

| SEQ ID NO: | Amino Acid Sequence | Toxicity |
|---|---|---|
|  | No peptide control | 0 |
| 1 | LLGDFFRKSKEKIGKEFKRIVQRIKDFLRNLVPRTES | ++ |
| 2 | RFGRFLRKIRRFRPKVTITIQGSARF | ++++ |
| 3 | RRWVQRWIRRWRPKV | + |

TABLE 5-continued

Toxicity of selected peptides.

| SEQ ID NO: | Amino Acid Sequence | Toxicity |
|---|---|---|
| 4 | RRWVQRWIRRWRKV | + |
| 5 | RRWVQRWIRRWRKPV | + |
| 6 | RRWVQRWIRRWRPWV | + |
| 7 | RRWVQRWIRRWRKWV | + |
| 8 | RRWVQRWIRRWRPK | + |
| 9 | RRWVQRWIRRWRPKW | + |
| 10 | RRWVQRWIRRWRPKVAAARRWV | + |
| 11 | RRWVQRWIRRWRPKRIVQRIKDFLRNLV | + |
| 12 | RRWVQRWIRRWRPKVAAARRWVQRWIRRWRPKV | ++ |
| 13 | RRWVQRWIRRWRKVAAARRWVQRWIRRWRPKV | ++++ |
| 14 | RRWVQRWIRRWRPKVLQKKGI | + |
| 15 | RRWVQRWIRRWRPKVLQKKGI | + |
| 16 | RRWVQRWIRRWRPKLQKKGI | + |
| 17 | APKAMRRWVQRWIRRWRPRV | + |
| 18 | APKAMRRWVQRWIRRWRPKVLQKKGI | + |
| 19 | APKAMRRWVQRWIRRWRPRLQKKGI | + |
| 20 | APKAMRRWVQRWIRRWRPLQKKGI | ++ |
| 21 | APKAMRRWVQRWIRRWRPKVLQKNNYL | + |
| 22 | APKAMRRWVQRWIRRWRPKVFQVTGSSA | + |
| 23 | APKAMRRWVQRWIRRWRPKVLLHYPSQKF | ++ |
| 25 | RRWVRRWIRRWRPKV | + |
| 26 | APKAMRWVQRWIRRWRPKLQKKGI | ++ |
| 27 | APKAMWVQRWIRRWRPLQKKGI | + |

(*): "0", no toxicity;
"+", weakly toxic;
"++", moderately toxic;
"+++", toxic;
"++++", very toxic.

We found that a number of the peptides as disclosed herein were only weakly toxic (score + in Table 5), while still exhibiting a high antimicrobial activity. This makes these peptides particularly suited for use as a medicament in the treatment of a microbial disease, such as in the treatment of a microbial infection. Whereas the prior art peptides were more toxic and less active as antimicrobial agent (such as LL-37; peptide according to SEQ ID NO: 1) or extremely toxic (such as CMAP-27; peptide according to SEQ ID NO: 2), the peptides according to the invention provide a palette of opportunities for the treatment of microbial diseases wherein the peptide can be custom-made to suit the needs of the patient. The optimal balance between toxicity and antimicrobial activity can be found by slightly modifying the amino acids adjacent to the amino acid sequence RRWVQRWIRRWR (SEQ ID NO: 24), or by modifying one or two amino acids from the peptide with an amino acid sequence RRWVQRWIRRWR (SEQ ID NO: 24) or its analogues.

We also tested some of the anti-microbial peptides against other bacteria (example 5, table 6). This again confirmed that the peptides as disclosed herein have a strong antimicrobial activity. It also shows that the peptides as disclosed herein have a broad spectrum of activity.

TABLE 6

Antimicrobial activity of various peptides against a number of different bacteria (*).

| SEQ ID NO: | Amino Acid Sequence | Dolosigranulum Pigrum | Moraxella nonliquefaciens | Enterobacter cloacae | Burkholderia cenocepacia | Salmonella typhimurium | Escherichia coli | Acinetobacter baumannii |
|---|---|---|---|---|---|---|---|---|
| 7 | RRWVQRWIRRWRKWV | + | ++++ | +++ | ++ | +++ | + | +++ |
| 11 | RRWVQRWIRRWRPKRIVQRIKDFLRNLV | ++++ | ++++ | ++++ | +++ | n.a. | n.a. | n.a. |
| 12 | RRWVQRWIRRWRPKVAAARRWVQRWIRRWRPKV | n.a. | n.a. | n.a. | n.a. | ++++ | +++ | +++ |
| 13 | RRWVQRWIRRWRKVAAARRWVQRWIRRWRPKV | ++++ | ++++ | ++++ | ++++ | n.a | n.a | n.a |

| SEQ ID NO | Amino Acid Sequence | Klebsiella pneumoniae | Achromobacter xylosoxidans | Stenotrophomonas maltophilia | Enterococcus faecium | Bacillus cereus | Staphylococcus haemolyticus | Listeria monocytogenes |
|---|---|---|---|---|---|---|---|---|
| 7 | RRWVQRWIRRWRKWV | + | ++ | +++ | + | +++ | ++++ | ++++ |
| 11 | RRWVQRWIRRWRPKRIVQRIKDFLRNLV | n.a. | n.a. | n.a. | n.a. | n.a | n.a | n.a |

TABLE 6-continued

Antimicrobial activity of various peptides against a number of different bacteria (*).

| | | | | | | | | |
|---|---|---|---|---|---|---|---|---|
| 12 | RRWVQRWIRRWRPKVAAARRWVQRWIRRWRPKV | +++ | ++ | ++++ | +++ | ++++ | ++++ | ++++ |
| 13 | RRWVQRWIRRWRKVAAARRWVQRWIRRWRPKV | n.a | n.a | n.a | n.a | n.a | n.a | n.a |

* Killing efficacy of peptides was determined and defined as follows: no colonies present after treatment with indicated concentration-range of peptides: "0", no killing; "+", killing when exposed to 10-20 µM peptides; "++", 5-10 µM; "+++"; 2-5 µM"; "++++", 0-2 µM; n.a., not analyzed.

The peptides of the invention may be used alone, or in combination. They may also be used in the form of multimers. Suitable combinations of peptides of the invention comprise concatemers of peptides of the invention serially coupled to each other via spacers, for instance in the form of a peptide dimer, a peptide trimer, etc., wherein the individual peptides are subsequently aligned. Single peptide or peptidomimetic chains may be coupled to a biocompatible protein, such as human serum albumin, humanized antibody, liposome, micelle, synthetic polymer, nanoparticle, and phage. Alternatively, multimers of individually combined peptides of the invention may be prepared in the form of dendrimers, or clusters, wherein three or more peptides are linked to one common centre.

Yet other combinations in the form of multimers may be formed by beads on the surface of which the peptides of the invention are exposed. The bead may then function as a carrier for the peptide, and may similarly function as a detectable label. Multimers can, for example, be prepared by biotinylating the N-terminus of peptide chains and subsequent complexation with streptavidin. As streptavidin is able to bind 4 biotin molecules or conjugates with high affinity, very stable tetrameric peptide complexes can be formed by this method. Multimers may be composed of identical or different peptides or peptidomimetics. Multimers of peptides according to the invention may thus be formed. Alternatively, peptides may be used as monomers in various combinations. Preferably, however, the multimers of the invention are composed of two or more peptides or peptidomimetics, in which each component constitutes to one asset of the total biocidal activity (targeting, antimicrobial activity, scavenging).

A pharmaceutical composition of the invention comprises a therapeutically effective amount of one or more peptides of the present invention. Once formulated, the pharmaceutical compositions of the invention can be administered directly to the subject in a method of treating bacterial infection comprising administering to a subject in need thereof a therapeutically effective amount of the composition of the invention.

Direct delivery of the compositions will generally be accomplished by topical application or other forms of administration, including orally, parenterally, subcutaneously, intradermally, sublingually, intralesionally, intraperitoneally, intravenously, intranasal or intramuscularly, pulmonary, or delivered to the interstitial space of a tissue.

The pharmaceutical composition may also comprise a suitable pharmaceutically acceptable carrier or diluent and may be in the form of a capsule, tablet, lozenge, dragee, pill, droplet, suppository, powder, spray, vaccine, ointment, paste, cream, inhalant, patch, aerosol, and the like. As pharmaceutically acceptable carrier, any solvent, diluent or other liquid vehicle, dispersion aid, surface active agent, isotonic agent, thickening or emulsifying agent, preservative, encapsulating agent, solid binder or lubricant can be used which is most suited for a particular dosage form and which is compatible with the peptide or peptide conjugate.

The pharmaceutical composition may further comprise other pharmaceutically active ingredients or ingredients that can neutralize or diminish inhibitory activity of certain compounds. For example, EDTA may be added to complex divalent cations that may otherwise inhibit the activity of certain peptides, if and when necessary.

A pharmaceutical composition may thus contain a pharmaceutically acceptable carrier. The term "pharmaceutically acceptable carrier" also includes a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Salts of peptides or functional equivalents are prepared by known methods, which typically involve the mixing of the peptide with either a pharmaceutically acceptable acid to form an acid addition salt, or with a pharmaceutically acceptable base to form a base addition salt. Whether an acid or a base is pharmaceutically acceptable can be easily decided by a person skilled in the art after taking the specific intended use of the compound into consideration. For instance, not all acids and bases that are acceptable for ex vivo applications can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. Moreover, also pharmaceutically acceptable solvates are encompassed.

Pharmaceutically acceptable salts can be used as disclosed herein. For example, mineral acid salts may be used such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

The peptides as disclosed herein or their analogues may be administered alone or in combination with pharmaceutically acceptable carriers or diluents by the routes previously indicated and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques known to those skilled in the art. Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition. Even more preferred administration routes are parenterally, subcutaneously, topically, intradermally, sublingually, intralesionally, intraperitoneally, intravenously, intranasal or intramuscularly, pulmonary, or delivered to the interstitial space of a tissue.

The active compounds may also be administered in the form of liposome delivery systems, such as small unilamellar vesicles, large unilamellar vesicles and multilamellar vesicles. Liposomes can be formed from a variety of (phospho)lipids, such as cholesterol, stearylamine or phosphatidylcholines. The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyphenyleneoxide-polylysine substituted with palmitoylresidues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels. For therapeutic treatment, the peptide or peptide-conjugate may be produced as described above and applied to the subject in need thereof. The peptide or peptide-conjugate may be administered to a subject by any suitable route, preferably in the form of a pharmaceutical composition adapted to such a route and in a dosage that is effective for the intended treatment.

Pharmaceutical compositions of this invention may contain other active agents, such as conventional antibiotics (like e.g. vancomycin, streptomycin, tetracyclin, penicillin) or other antimicrobial compounds, such as antivirals, antifungals, e.g. itraconazole or myconazole. Also compounds that alleviate other infection symptoms, such as fever (e.g. salicylic acid) or skin rash may be added.

Effectivity of the peptides according to the invention against viruses was determined in a model system employing influenza A virus (example 7). The results are shown in FIGS. 3-7. It appeared that the peptides as described herein were also active as antiviral agents and they may therefore be used in the treatment of viral diseases.

Therapeutically effective dosages of the peptide or peptide-conjugate required for treating a bacterial or viral infection in the body of a human or animal subject, can easily be determined by the skilled person, for instance by using animal models.

The term "therapeutically effective amount" as used herein refers to an amount of a therapeutic peptide or peptide-conjugate according to the present invention, to reduce or prevent growth and colonization of bacteria, or to exhibit a detectable therapeutic or prophylactic effect. The effect can be detected by, for example, culturing biopsies and assaying for bacterial activity or by any other suitable method of assessing the progress or severity of bacterial infection. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgment of the clinician or experimenter. Specifically, the compositions of the present invention can be used to reduce or prevent bacterial infection and/or accompanying biological or physical manifestations, such as reduction of fever. Methods that permit the clinician to establish initial dosages are known in the art. The dosages determined to be administered must be safe and efficacious.

For purposes of the present invention, an effective dose will be from about 0.01 µg/kg to 50 mg/kg, preferably 0.5 µg/kg to about 10 mg/kg of the peptide or peptide-conjugate in the individual to which it is administered. Dosages for achieving the therapeutic effects of the pharmaceutical composition described herein may easily be determined by the skilled person.

Yet in another alternative embodiment, the peptide or peptide-conjugate or compositions of the invention may be administered from a controlled or sustained release matrix inserted in the body of the subject.

It may also be advantageous to administer a compound of the invention in a transmucosal dosage form. This route of administration is non-invasive and thus less cumbersome for the subject that is being treated and for the person that is providing the treatment; at the same time it may lead to an improved bioavailability of the compound compared to oral administration, especially if the compound is not stable in the fluids of the digestive system, or if it is too large to be absorbed from the gut effectively. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets.

Preferably, the excipients used for a transmucosal dosage form include one or more substances providing for mucoadhesion, thus prolonging the contact time of the dosage form with the site of absorption and thereby potentially increasing the extent of absorption.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, topical, or ocular administration may also be feasible in some cases.

In a preferred embodiment, the peptides according to the invention may advantageously be used in the treatment of cystic fibrosis (CF), chronic obstructive pulmonary disease (COPD) and non-CF bronchiectasis. There is a great need in the art for antibiotics that can be applied locally. This is in particular because the peptides according to the invention have surprisingly good dose-effect ratios.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This may be achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, cholesterol and its derivatives, ethanol, fatty acids, oleic acid, fatty acid derivatives, EDTA, carbomers, polycarbophil, and chitosan.

Indications for which the peptides of the invention can be used are bacterial infections by both Gram-positive and Gram-negative bacteria, such as *E. coli, Agrobacterium tumefaciens, Salmonella typhimurium, Erwinia carotovora, E. herbicola, E. chrysanthemi, Klebsiella pneumoniae, Haemophilus influenzae, Francisella tularensis, Archanobacterium pyogenes, Avibacterium paragallinarum, Bacillus anthracis, Bacillus megaterium, Bacillus anthracis, Bordetella* spp., *Brachyspira* spp., *Brucella* spp., *Campylobacter* spp., *Clostridium botulinum, Clostridium perfringens, Clostridium septicum, Corynebacterium pyogenes, Coxiella burnetii, Enterococcus* spp., *Haemophilus somnus, Yersinia pestis, Listeria monocytogenes, Mannheimia haemolytica, Mycobacterium tuberculosis, Mycobacterium avium, Mycoplasma gallisepticum, Mycoplasma synoviae, Ornithobacterium rhinotracheale, Pasteurella aeruginosa, Pasteurella multocida, Pneumococcus* spp, *Stenotrophomonas maltophilia, Achromobacter xylosoxidans, Burholderia* species, *Pseudomonas aeruginosa, Riemerella anatipestifer, Salmonella* spp., *Streptococcus uberis, Streptococcus* spp., *Staphylococcus aureus, Staphylococcus pyrogenes, Truperella pygoenes, Vibria cholerae, Micrococcus luteus, Moraxella, Neisseria ghonnorhoea, Aerobacter* or *Borrelia*.

Apart from the above diseases, the peptides as disclosed herein and their analogues as described herein may be used to treat a disease or bacterial infection selected from the list consisting of *Acinetobacter baumannii* infection, Actinomycosis, Acute prostatitis, *Aeromonas hydrophila*, Anaerobic infection, Bacillary peliosis, Bacteremia, Bacterial cold water disease, Bacterial kidney disease, Bacterial pneumonia, Bacterial soft rot, *Bacteroides ureolyticus*, Baggio-Yoshinari syndrome, Barcoo fever, Bartonellosis, Biliary fever, Botryomycosis, Bovine Campylobacteriosis, Brazilian purpuric fever, Brodie abscess, *Burkholderia cepacia* complex, Buruli ulcer, Campylobacteriosis, *Capnocytophaga canimorsus*, Cariogram, Carrion's disease, CC398, Centor criteria, *Chlamydia* research, *Chlamydia suis*, Cholera, Chronic bacterial prostatitis, Chronic recurrent multifocal osteomyelitis, Combined periodontic-endodontic lesions, Contagious bovine pleuropneumonia, Copper-silver ionization, Digital dermatitis, Diphtheria, Diphtheritic stomatitis, *Edwardsiella ictaluri, Edwardsiella tarda*, Ehrlichiosis (canine), Enteroinvasive *Escherichia coli*, Epidural abscess, Epiglottitis, Erysipelas, European Working Group for Legionella Infections, Far East scarlet-like fever, Fitz-Hugh-Curtis syndrome, Foot rot, *Gardnerella vaginalis*, Garre's sclerosing osteomyelitis, Gram-negative bacterial infection, Gram-positive actinobacteria diseases, Granuloma inguinale, Haemophilus meningitis, Human monocytotropic ehrlichiosis, Hundred days' cough, Interdigital dermatitis in cattle, *Legionella*, Lemierre's syndrome, Leprosy, Listeriosis, Lyme disease, Meningococcal disease, Methicillin-resistant *Staphylococcus aureus, Mycobacterium, Mycobacterium avium*-intracellular infection, *Mycoplasma adleri, Mycoplasma agalactiae, Mycoplasma amphoriforme, Mycoplasma hyorhinis, Mycoplasma pneumonia, Mycoplasma synoviae*, Nanobacterium, Necrotizing fasciitis, Nocardiosis, Noma (disease), Nontuberculous mycobacteria, Omphalitis of newborn, Orbital cellulitis, Ornithobacterium rhinotracheale, Osteomyelitis, Overwhelming post-splenectomy infection, Paget's abscess, *Pasteurella anatis, Pasteurella canis, Pasteurella dagmatis, Pasteurella langaa, Pasteurella multocida, Pasteurella stomatis*, Pathogenic bacteria, Pelvic inflammatory disease, Tubo-ovarian abscess, *Peptostreptococcus anaerobius, Peptostreptococcus asaccharolyticus*, Periodontal abscess, Periorbital cellulitis, Peritonsillar abscess, Pertussis, Pneumococcal pneumonia, Porcine intestinal spirochaetosis, Pott disease, *Prevotella bivia*, Proctitis, Proteus OX19, Pseudomonas infection, Psittacosis, Pyaemia, Pyomyositis, Q fever, Relapsing fever, Retropharyngeal abscess, *Riemerella anatipestifer*, Salmonellosis, *Serratia* infection, Shigellosis, Southern tick-associated rash illness, Staphylococcal scalded skin syndrome, *Staphylococcus aureus*, Swine brucellosis, Syphilis, Syphilitic aortitis, Tetanus, Toxic shock syndrome, Trench fever, Tropical ulcer, Urogenital tuberculosis, Vaginal microbiota, Vancomycin-resistant *Staphylo-* coccus aureus, Vertebral osteomyelitis, Vibrio vulnificus, Waterhouse-Friderichsen syndrome, Widal test, Xanthogranulomatous osteomyelitis, Yersinia pestis and Yersiniosis.

Apart from bacterial infections, also other infections, like infections with viruses, fungi, yeasts and parasites may be treated with the peptides of the invention.

Next to therapeutic use for treatment of infections, it is also possible to use the antibiotic or antimicrobial peptides of the invention in a bactericidal composition that can be used to clean surfaces and/or equipment. Another field of application is in packaging, where peptides can be linked to or embedded in packaging material for packaging of food or other material that is easily degradable by micro-organisms. Yet another field of application is the coating of implants and the prevention of biofilms.

In a particular advantageous embodiment of the invention, peptides according to the invention as disclosed herein are used in packaging applications. It is particularly desired that the toxicity of such peptides is as little as possible, preferably, the peptides are not toxic.

FIGURE LEGEND

FIG. 1: diagram showing the antimicrobial activity against *Pseudomonas aeruginosa* of several analogues of the peptide according to SEQ ID NO: 7 wherein the amino acids of the core sequence according to SEQ ID NO: 24 (x-axis) were replaced by an alanine residue.

FIG. 2: diagram showing the antimicrobial activity against *Staphylococcus aureus* of several analogues of the peptide according to SEQ ID NO: 7 wherein the amino acids of the core sequence according to SEQ ID NO: 24 (x-axis) were replaced by an alanine residue.

FIGS. 3-7: Graphs showing the anti-viral activity of peptides according to SEQ ID NO: 7, 10, 11, 12 and 13. Peptide-mediated neutralization of influenza A virus (Aichi68 strain) was tested using infection of MDCK cells. Shown is the reduction of infection (% of control, no peptide added) as a function of peptide concentration (0-0.25-0.5-1.0 µM). Values are mean±SEM of four experiments. *, $p<0.05$; **, $p<0.005$ compared to virus only. Statistical analysis was carried out by the Student's t-test.

EXAMPLES

Example 1: Killing Assay

The *Pseudomonas aeruginosa* and *Staphylococcus aureus* strains used in this study were obtained from ATCC (strain 27853 and strain 29213, respectively) or isolated from Cystic Fibrosis patients (University Medical Center Utrecht, Utrecht, The Netherlands).

All bacterial strains were grown in Tryptone Soy Broth (TSB; Oxoid Limited, Hampshire, UK) and on Tryptone Soy Agar (TSA; Oxoid Ltd). For all experiments bacteria were inoculated and grown overnight in TSB at 37° C. The next day bacteria were transferred to a fresh TSB tube and grown to mid-logarithmic phase.

The bacterial killing assay was performed by colony count as follows: logarithmic phase cultures of bacteria were washed once in TSB and diluted to 2×10E6 CFU/ml. Subsequently, bacteria were exposed to peptides (5 µM final concentration, 1×10E6 CFU/ml) for 3 h at 37° C. To this end, various incubation media were used as indicated:

'MHB', Mueller Hinton Broth;
'BEPC', Bronchial Epithelial Cell Medium;
'NaCl 7.4', MHB+0.9% NaCl pH 7.4;
'NaCl 6.5', MHB+0.9% NaCl pH 6.5.

In the absence of peptides, the bacterial density developed into approximately 1×10E8 CFU/ml after 3 h at 37° C. in all media tested. Afterwards, the mixtures were serially diluted 10-10,000 fold and 15 microliter of each dilution was applied on TSA plates.

After drying, the plates were incubated overnight at 37° C. Bacterial survival was assessed by counting colonies (colony forming units, CFU's). Killing efficacy of peptides was determined and defined as follows: "0", no killing; "+", 0-100 fold reduction in CFU's after treatment; "++", 100-1.000 fold; "+++"; 1.000-100.000 fold; "++++", no CFU's detected (N.a. not analyzed).

Example 2: Bioscreen Assay

Bacteria (2×10E6 CFU/ml) were suspended in MHB+ 0.9% NaCl and were mixed 1:1 (vol/vol) with peptides dissolved in the same medium in various concentrations (final conc. 0-10 µM) and added to Bioscreen C analyzer plates (Oy Growth Curves Ab Ltd., Helsinki, Finland) and incubated for 18 h at 37° C. while shaking (200 rpm) in a Bioscreen C analyzer (Oy Growth Curves Ab Ltd). The OD (600 nm) was measured every 15 min. Minimal Inhibitory Concentrations (MIC values) were assessed for each peptide. The results are provided as the lowest concentration tested that resulted in no growth after 18 h.

Example 3: Antifungal Activity

Antifungal activity of the peptides was tested on two lab strains of *Aspergillus fumigatus* (CEA10 and Af293) as well as on 16 different *Aspergillus fumigatus* strains isolated from CF patients (University Medical Center Utrecht, Utrecht, The Netherlands).

Cells were first grown on potato dextrose agar (PDA) plates at 37° C. for 4 days as previously described (1). The resting spores were harvested and washed and resulting spore solutions contained over 20 million spores per ml and were frozen until use, or stored for a maximum of 5 days at 4° C. The concentration of spore solution used in the metabolic activity assay was set to 1×10E6 spores/ml.

Peptide dilutions (2-5 µM, 45 µl) were applied into the wells of polystyrene flat bottom NON-binding 96 wells plates. Subsequently, a mix containing 50 µl of 0.125× Minimal Medium (salts only) with 2% glucose at pH 7.0, 5 µl spore solution (1×10E6 spores/ml) and 5 µl resazurin (2100 µM, Sigma R7017)), was added to each well that contained peptide or sterile H2O (positive control for growth). For the negative control sterile $H_2O$ was used to replace the spore solution and peptide. Plates were incubated at 37° C. for 48 hours, and resazurin conversion, indicative for the viability/metabolic activity of the fungal spores, was measured at OD570 nm with Multiskan EX microplate reader at time points 20-24 and 48 hours.

The results obtained with the two lab strains were identical.

Relative potency of peptides to inhibit the metabolic activity of fungal spores was defined as follows: "0", no inhibition; "+", 0-25% reduction in metabolic activity; "++", 25-50%; "+++", 50-75%; "++++", 75-100%.

The results could be confirmed when either one of the 16 strains isolated from a CF patient was used. No discrepancies were observed when using a lab strain or any of the 16 isolates.

Example 4: Toxicity Measurements

The cytotoxic effect of all peptides was determined as previously described (2) using primary human nasal epithelial cells, obtained by nasal brushing of healthy individuals.

Cells were grown to confluence in 96-well plates in Bronchial Epithelial Cell Growth Medium (BEPC, Lonza) at 37° C. and 5% CO2. Peptides were diluted in the same medium to a final concentration of 5 µM and applied to the washed (PBS, twice) cells and incubated for 3 hours or 24 hours at 37° C. After incubation, the medium was removed, cells were washed twice (PBS) and fresh BEPC containing 10% (v/v) cell proliferation reagent WST-1 (Roche) was added to each well.

Conversion of WST-1 is indicative for cell viability and reduced conversion by cells is a measure for cytotoxic effects exerted by peptides. After incubation for 30 minutes at 37° C. the absorbance of each well was measured at 450 nm and 650 nm (reference wavelength). Controls included cells exposed to peptide-free medium (set to 100% WST-1 conversion) and wells without cells (background). Results are based upon 5 individual experiments and defined as follows: "0", no toxicity; "+", weakly toxic; "++", moderately toxic; "+++", toxic; "++++", very toxic.

Example 5: Activity Against a Variety of Bacteria

The bacterial strains used in this study were obtained from University Medical Center Utrecht, Utrecht, The Netherlands. All bacterial strains were grown in Tryptone Soy Broth (TSB; Oxoid Limited, Hampshire, UK) and on Tryptone Soy Agar (TSA; Oxoid Ltd). For all experiments bacteria were inoculated and grown overnight in TSB at 37° C. The next day bacteria were transferred to a fresh TSB tube and grown to mid-logarithmic phase.

The bacterial killing assay was performed by colony count as follows: logarithmic phase cultures of bacteria were washed once in DMEM+1% fetal calf serum (FCS) and diluted to 2×10E6 CFU/ml. Subsequently, 1×10E6 CFU/ml bacteria were exposed to peptides in a final concentration of 0, 2, 5 and 10 µM, for 3 h at 37° C.

In the absence of peptides, the bacterial density developed into approximately 1×10E8 CFU/ml after 3 h at 37° C. Afterwards, the mixtures were serially diluted 10-10,000 fold and 15 microliter of each dilution was applied on TSA plates by track dilution.

After drying, the plates were incubated overnight at 37° C. Bacterial survival was assessed by counting colonies. Killing efficacy of peptides was determined and defined as follows: no colonies present after treatment with indicated concentration-range of peptides: "0", no killing; "+", killing when exposed to 10-20 µM peptides; "++", 5-10 µM; "+++", 2-5 µM", "++++", 0-2 µM (N.a. not analyzed).

Example 6: Alanine Scan of Peptide 7

The peptide with an amino acid sequence according to SEQ ID NO: 7 was subjected to an alanine scan. Peptides were commercially obtained from ChinaPeptides Co. Ltd.

The amino acids of the core sequence according to SEQ ID NO: 24 were one-by-one replaced by an alanine residue and the individual peptides were tested for their anti-microbial activity against *Staphylococcus aureus* and *Pseudomonas aeruginosa* as described in Example 1. Specific conditions used were: Peptide concentration: 8 µM; Medium: MHB+ 0.9% NaCl. Experiments were performed in triplicate. Average results and standard deviations are shown in FIGS. 1 and 2.

Example 7: Antiviral Activity

Antiviral activity of the peptides was tested by neutralization of infectivity using Madin-Darby canine kidney (MDCK) cell monolayers. Peptides were tested for their antiviral potency against pandemic influenza A virus strain A/Aichi/68(H3N2) (Aichi68), obtained from American Type Culture Collection (ATCC, Manassas, Va.) and was grown in the chorioallantoic fluid of 10-day-old chicken eggs and purified on a discontinuous sucrose gradient.

MDCK cell monolayers (American Type Culture Collection, Manassas, Va.) were prepared in 96 well plates and grown to confluency. These cell layers were then infected with diluted influenza A virus preparations for 45 min. at 37° C. Before adding to cell layers, Aichi68 was pre-incubated for 30 min. at 37° C. with various concentrations of peptides or control buffer. Peptides according to SEQ ID NO's: 7, 10, 11, 12 and 13 were used. The multiplicity of infection (MOI) was approximately 0.1. MOI and was calculated based on number of cells at confluence. After 45 min, the plates were washed, followed by 24 hrs incubation at 37° in culture medium. After 24 hrs, MDCK cells were washed with PBS and fixed and stained for the presence of IAV infected cells using a primary mouse monoclonal antibody (1:100 dilution) directed against the influenza A viral nucleoprotein (EMD Millipore, MA). A rhodamine labeled secondary (1:1000) antibody (EMD Millipore, MA) was used to detect primary antibody. Fluorescent positive cells were counted visually on a fluorescent microscope (Nikon MVI, Avon, Mass., US). The number of fluorescent infectious foci per ml of inoculum was calculated from this. We expressed the data as mean±SEM % of control (n=4) to make relative comparisons between the peptides tested. Statistical comparisons were made using Student's unpaired, two-tailed t test.

The results are shown in FIGS. 3-7.

REFERENCES

1. Escobar N, Ordonez S R, Wösten H A, Haas P J, de Cock H, Haagsman H P; Hide, keep quiet, and keep low: properties that make *Aspergillus fumigatus* a successful lung pathogen; Front Microbio.2016 Apr. 6; 7:438. doi: 10.3389/fmicb.2016.00438. eCollection 2016.
2. Veldhuizen E J, Schneider V A, Agustiandari H, van Dijk A, Tjeerdsma-van Bokhoven J L, Bikker F J, Haagsman H P; Antimicrobial and immunomodulatory activities of PR-39 derived peptides; PLoS One. 2014 Apr. 22; 9(4): e95939. doi: 10.1371/journal.pone.0095939. eCollection 2014.

The invention claimed is:

1. A peptide with antimicrobial activity, wherein the peptide consists of the general amino acid sequence X1-X2-X3, wherein X1 is 0-5 amino acids, X2 is the amino acid sequence RRWVQRWIRRWR (SEQ ID NO: 24), and X3 is 2-21 amino acids.

2. A pharmaceutical composition comprising the peptide of claim 1 and a pharmaceutically acceptable carrier or excipient.

3. A method of treating, preventing, or ameliorating a microbial infection in an animal, the method comprising:
administering to the animal the peptide of claim 1.

4. The method according to claim 3, wherein the microbial infection is selected from the group consisting of cystic fibrosis, bacterial infections, fungal infections, viral infections, chronic pulmonary inflammation, respiratory tract infections, chronic obstructive pulmonary disease (COPD), non-CF bronchiectasis, yeast infections, and parasite infections.

5. The method according to claim 3 wherein the animal is a human.

6. A method of decreasing the amount of microorganisms, the method comprising:
administering to the microorganisms the peptide of claim 1.

7. The method according to claim 6 wherein the amount of microorganisms in solution or on a solid surface is decreased.

8. The method according to claim 6 wherein the microorganisms are eradicated or killed.

* * * * *

SEQUENCE LISTING

<160> NUMBER OF SEQ ID NOS: 39

<210> SEQ ID NO 1
<211> LENGTH: 37

<212> TYPE: PRT
<213> ORGANISM: homo sapiens

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 2
<211> LENGTH: 26
<212> TYPE: PRT
<213> ORGANISM: homo sapiens

<400> SEQUENCE: 2

Arg Phe Gly Arg Phe Leu Arg Lys Ile Arg Arg Phe Arg Pro Lys Val
1               5                   10                  15

Thr Ile Thr Ile Gln Gly Ser Ala Arg Phe
            20                  25

<210> SEQ ID NO 3
<211> LENGTH: 15
<212> TYPE: PRT
<213> ORGANISM: homo sapiens

<400> SEQUENCE: 3

Arg Arg Trp Val Gln Arg Trp Ile Arg Arg Trp Arg Pro Lys Val
1               5                   10                  15

<210> SEQ ID NO 4
<211> LENGTH: 14
<212> TYPE: PRT
<213> ORGANISM: homo sapiens

<400> SEQUENCE: 4

Arg Arg Trp Val Gln Arg Trp Ile Arg Arg Trp Arg Lys Val
1               5                   10

<210> SEQ ID NO 5
<211> LENGTH: 15
<212> TYPE: PRT
<213> ORGANISM: homo sapiens

<400> SEQUENCE: 5

Arg Arg Trp Val Gln Arg Trp Ile Arg Arg Trp Arg Lys Pro Val
1               5                   10                  15

<210> SEQ ID NO 6
<211> LENGTH: 15
<212> TYPE: PRT
<213> ORGANISM: homo sapiens

<400> SEQUENCE: 6

Arg Arg Trp Val Gln Arg Trp Ile Arg Arg Trp Arg Pro Trp Val
1               5                   10                  15

<210> SEQ ID NO 7
<211> LENGTH: 15
<212> TYPE: PRT
<213> ORGANISM: homo sapiens

<400> SEQUENCE: 7

-continued

Arg Arg Trp Val Gln Arg Trp Ile Arg Trp Arg Lys Trp Val
1               5                   10                  15

<210> SEQ ID NO 8
<211> LENGTH: 14
<212> TYPE: PRT
<213> ORGANISM: homo sapiens

<400> SEQUENCE: 8

Arg Arg Trp Val Gln Arg Trp Ile Arg Trp Arg Pro Lys
1               5                   10

<210> SEQ ID NO 9
<211> LENGTH: 15
<212> TYPE: PRT
<213> ORGANISM: homo sapiens

<400> SEQUENCE: 9

Arg Arg Trp Val Gln Arg Trp Ile Arg Trp Arg Pro Lys Trp
1               5                   10                  15

<210> SEQ ID NO 10
<211> LENGTH: 22
<212> TYPE: PRT
<213> ORGANISM: homo sapiens

<400> SEQUENCE: 10

Arg Arg Trp Val Gln Arg Trp Ile Arg Trp Arg Pro Lys Val Ala
1               5                   10                  15

Ala Ala Arg Arg Trp Val
            20

<210> SEQ ID NO 11
<211> LENGTH: 28
<212> TYPE: PRT
<213> ORGANISM: homo sapiens

<400> SEQUENCE: 11

Arg Arg Trp Val Gln Arg Trp Ile Arg Trp Arg Pro Lys Arg Ile
1               5                   10                  15

Val Gln Arg Ile Lys Asp Phe Leu Arg Asn Leu Val
            20                  25

<210> SEQ ID NO 12
<211> LENGTH: 33
<212> TYPE: PRT
<213> ORGANISM: homo sapiens

<400> SEQUENCE: 12

Arg Arg Trp Val Gln Arg Trp Ile Arg Trp Arg Pro Lys Val Ala
1               5                   10                  15

Ala Ala Arg Arg Trp Val Gln Arg Trp Ile Arg Trp Arg Pro Lys
            20                  25                  30

Val

<210> SEQ ID NO 13
<211> LENGTH: 32
<212> TYPE: PRT
<213> ORGANISM: homo sapiens

<400> SEQUENCE: 13

Arg Arg Trp Val Gln Arg Trp Ile Arg Trp Arg Lys Val Ala Ala

```
                1               5                  10                  15
Ala Arg Arg Trp Val Gln Arg Trp Ile Arg Arg Trp Arg Pro Lys Val
                20                  25                  30
```

<210> SEQ ID NO 14
<211> LENGTH: 21
<212> TYPE: PRT
<213> ORGANISM: homo sapiens

<400> SEQUENCE: 14

```
Arg Arg Trp Val Gln Arg Trp Ile Arg Arg Trp Arg Pro Lys Val Leu
1               5                   10                  15
Gln Lys Lys Gly Ile
                20
```

<210> SEQ ID NO 15
<211> LENGTH: 21
<212> TYPE: PRT
<213> ORGANISM: homo sapiens

<400> SEQUENCE: 15

```
Arg Arg Trp Val Gln Arg Trp Ile Arg Arg Trp Arg Pro Lys Val Leu
1               5                   10                  15
Gln Lys Lys Gly Ile
                20
```

<210> SEQ ID NO 16
<211> LENGTH: 20
<212> TYPE: PRT
<213> ORGANISM: homo sapiens

<400> SEQUENCE: 16

```
Arg Arg Trp Val Gln Arg Trp Ile Arg Arg Trp Arg Pro Lys Leu Gln
1               5                   10                  15
Lys Lys Gly Ile
                20
```

<210> SEQ ID NO 17
<211> LENGTH: 20
<212> TYPE: PRT
<213> ORGANISM: homo sapiens

<400> SEQUENCE: 17

```
Ala Pro Lys Ala Met Arg Arg Trp Val Gln Arg Trp Ile Arg Arg Trp
1               5                   10                  15
Arg Pro Arg Val
                20
```

<210> SEQ ID NO 18
<211> LENGTH: 26
<212> TYPE: PRT
<213> ORGANISM: homo sapiens

<400> SEQUENCE: 18

```
Ala Pro Lys Ala Met Arg Arg Trp Val Gln Arg Trp Ile Arg Arg Trp
1               5                   10                  15
Arg Pro Lys Val Leu Gln Lys Lys Gly Ile
                20                  25
```

<210> SEQ ID NO 19
<211> LENGTH: 25
<212> TYPE: PRT

<213> ORGANISM: homo sapiens

<400> SEQUENCE: 19

Ala Pro Lys Ala Met Arg Arg Trp Val Gln Arg Trp Ile Arg Arg Trp
1               5                   10                  15
Arg Pro Arg Leu Gln Lys Lys Gly Ile
            20                  25

<210> SEQ ID NO 20
<211> LENGTH: 24
<212> TYPE: PRT
<213> ORGANISM: homo sapiens

<400> SEQUENCE: 20

Ala Pro Lys Ala Met Arg Arg Trp Val Gln Arg Trp Ile Arg Arg Trp
1               5                   10                  15
Arg Pro Leu Gln Lys Lys Gly Ile
            20

<210> SEQ ID NO 21
<211> LENGTH: 27
<212> TYPE: PRT
<213> ORGANISM: homo sapiens

<400> SEQUENCE: 21

Ala Pro Lys Ala Met Arg Arg Trp Val Gln Arg Trp Ile Arg Arg Trp
1               5                   10                  15
Arg Pro Lys Val Leu Gln Lys Asn Asn Tyr Leu
            20                  25

<210> SEQ ID NO 22
<211> LENGTH: 28
<212> TYPE: PRT
<213> ORGANISM: homo sapiens

<400> SEQUENCE: 22

Ala Pro Lys Ala Met Arg Arg Trp Val Gln Arg Trp Ile Arg Arg Trp
1               5                   10                  15
Arg Pro Lys Val Phe Gln Val Thr Gly Ser Ser Ala
            20                  25

<210> SEQ ID NO 23
<211> LENGTH: 29
<212> TYPE: PRT
<213> ORGANISM: homo sapiens

<400> SEQUENCE: 23

Ala Pro Lys Ala Met Arg Arg Trp Val Gln Arg Trp Ile Arg Arg Trp
1               5                   10                  15
Arg Pro Lys Val Leu Leu His Tyr Pro Ser Gln Lys Phe
            20                  25

<210> SEQ ID NO 24
<211> LENGTH: 12
<212> TYPE: PRT
<213> ORGANISM: homo sapiens

<400> SEQUENCE: 24

Arg Arg Trp Val Gln Arg Trp Ile Arg Arg Trp Arg
1               5                   10

<210> SEQ ID NO 25

```
<211> LENGTH: 15
<212> TYPE: PRT
<213> ORGANISM: homo sapiens

<400> SEQUENCE: 25

Arg Arg Trp Val Arg Arg Trp Ile Arg Arg Trp Arg Pro Lys Val
1               5                   10                  15

<210> SEQ ID NO 26
<211> LENGTH: 24
<212> TYPE: PRT
<213> ORGANISM: homo sapiens

<400> SEQUENCE: 26

Ala Pro Lys Ala Met Arg Trp Val Gln Arg Trp Ile Arg Arg Trp Arg
1               5                   10                  15

Pro Lys Leu Gln Lys Lys Gly Ile
            20

<210> SEQ ID NO 27
<211> LENGTH: 22
<212> TYPE: PRT
<213> ORGANISM: homo sapiens

<400> SEQUENCE: 27

Ala Pro Lys Ala Met Trp Val Gln Arg Trp Ile Arg Arg Trp Arg Pro
1               5                   10                  15

Leu Gln Lys Lys Gly Ile
            20

<210> SEQ ID NO 28
<211> LENGTH: 15
<212> TYPE: PRT
<213> ORGANISM: homo sapiens

<400> SEQUENCE: 28

Ala Arg Trp Val Gln Arg Trp Ile Arg Arg Trp Arg Lys Trp Val
1               5                   10                  15

<210> SEQ ID NO 29
<211> LENGTH: 15
<212> TYPE: PRT
<213> ORGANISM: homo sapiens

<400> SEQUENCE: 29

Arg Ala Trp Val Gln Arg Trp Ile Arg Arg Trp Arg Lys Trp Val
1               5                   10                  15

<210> SEQ ID NO 30
<211> LENGTH: 15
<212> TYPE: PRT
<213> ORGANISM: homo sapiens

<400> SEQUENCE: 30

Arg Arg Ala Val Gln Arg Trp Ile Arg Arg Trp Arg Lys Trp Val
1               5                   10                  15

<210> SEQ ID NO 31
<211> LENGTH: 15
<212> TYPE: PRT
<213> ORGANISM: homo sapiens

<400> SEQUENCE: 31

Arg Arg Trp Ala Gln Arg Trp Ile Arg Arg Trp Arg Lys Trp Val
```

```
1               5                   10                  15
```

<210> SEQ ID NO 32
<211> LENGTH: 15
<212> TYPE: PRT
<213> ORGANISM: homo sapiens

<400> SEQUENCE: 32

```
Arg Arg Trp Val Ala Arg Trp Ile Arg Arg Trp Arg Lys Trp Val
1               5                   10                  15
```

<210> SEQ ID NO 33
<211> LENGTH: 15
<212> TYPE: PRT
<213> ORGANISM: homo sapiens

<400> SEQUENCE: 33

```
Arg Arg Trp Val Gln Ala Trp Ile Arg Arg Trp Arg Lys Trp Val
1               5                   10                  15
```

<210> SEQ ID NO 34
<211> LENGTH: 15
<212> TYPE: PRT
<213> ORGANISM: homo sapiens

<400> SEQUENCE: 34

```
Arg Arg Trp Val Gln Arg Ala Ile Arg Arg Trp Arg Lys Trp Val
1               5                   10                  15
```

<210> SEQ ID NO 35
<211> LENGTH: 15
<212> TYPE: PRT
<213> ORGANISM: homo sapiens

<400> SEQUENCE: 35

```
Arg Arg Trp Val Gln Arg Trp Ala Arg Arg Trp Arg Lys Trp Val
1               5                   10                  15
```

<210> SEQ ID NO 36
<211> LENGTH: 15
<212> TYPE: PRT
<213> ORGANISM: homo sapiens

<400> SEQUENCE: 36

```
Arg Arg Trp Val Gln Arg Trp Ile Ala Arg Trp Arg Lys Trp Val
1               5                   10                  15
```

<210> SEQ ID NO 37
<211> LENGTH: 15
<212> TYPE: PRT
<213> ORGANISM: homo sapiens

<400> SEQUENCE: 37

```
Arg Arg Trp Val Gln Arg Trp Ile Arg Ala Trp Arg Lys Trp Val
1               5                   10                  15
```

<210> SEQ ID NO 38
<211> LENGTH: 15
<212> TYPE: PRT
<213> ORGANISM: homo sapiens

<400> SEQUENCE: 38

```
Arg Arg Trp Val Gln Arg Trp Ile Arg Arg Ala Arg Lys Trp Val
1               5                   10                  15
```

```
<210> SEQ ID NO 39
<211> LENGTH: 15
<212> TYPE: PRT
<213> ORGANISM: homo sapiens

<400> SEQUENCE: 39

Arg Arg Trp Val Gln Arg Trp Ile Arg Arg Trp Ala Lys Trp Val
1               5                   10                  15
```